United States Patent
Vaitkus

[11] Patent Number: 5,852,238
[45] Date of Patent: Dec. 22, 1998

[54] MEASURING DEVICE AND MEASURING METHOD

[75] Inventor: Rimantas Vaitkus, Vilnius, Lithuania

[73] Assignee: Semiconductor Energy Laboratory Co., Ltd., Kanagawa, Japan

[21] Appl. No.: 343,969

[22] Filed: Nov. 18, 1994

[30] Foreign Application Priority Data

Nov. 26, 1993 [JP] Japan ................................ 5-320936

[51] Int. Cl.$^6$ ........................................................ G01F 1/68
[52] U.S. Cl. ........................................................ 73/204.11
[58] Field of Search ............................ 73/204.16, 204.24, 73/204.25, 204.26, 202.5, 204.19

[56] References Cited

U.S. PATENT DOCUMENTS

| | | | |
|---|---|---|---|
| 3,085,431 | 4/1963 | Yerman et al. | 73/204 |
| 3,425,277 | 2/1969 | Adams | 73/204 |
| 3,942,378 | 3/1976 | Olmstead | 73/204 |
| 4,043,195 | 8/1977 | Hunting | 73/204 |
| 4,135,396 | 1/1979 | Stanke et al. | 73/204 |
| 4,888,988 | 12/1989 | Lee et al. | 73/204.26 |
| 5,144,380 | 9/1992 | Kimoto et al. | 357/22 |

*Primary Examiner*—Elizabeth L. Dougherty
*Assistant Examiner*—Jewel Artis
*Attorney, Agent, or Firm*—Sixbey, Friedman, Leedom & Ferguson, PC..; Gerald J. Ferguson, Jr.; Karlton C. Butts

[57] ABSTRACT

A pulse-like heating is applied to a thin-film material having a high thermal conductivity such as a diamond thin film so that a response characteristic at this time is measured as a change in temperature of the thin film. The response characteristic reflects the thermal influence of the circumstance on the thin-film material, and depends, for example, on the flow rate of fluid. At this time, a sensor for obtaining an output depending on the fluid and the temperature of the fluid and a sensor for obtaining an output corresponding to the temperature of fluid are prepared to compare and process both the output with the result of obtaining an output which reflects the flow rate with accuracy not depending on the temperature.

11 Claims, 10 Drawing Sheets

MEASURING DEVICE AND MEASURING METHOD

BACKGROUND OF THE INVENTION

1. Field of the Invention

The present invention relates to a measuring device and a measuring method which are not influenced by a change in temperature of an object to be measured or measuring environment by digitally compensating a temperature.

The measuring device and measuring method of the present invention can be used for an object to be measured stated below.

1) Measurement of a flow rate or flow velocity;
2) Measurement of the thermal conductivity or specific heat of fluid;
3) Discrimination of fluid;
4) Measurement of a ratio of mixing a plurality of fluids;
5) Measurement of the concentration of material contained in fluid (for example, measurement of humidity).

Further, a difference in the thermal conductivity or the specific heat of material to be measured (irrespective of gas, liquid or solid) can be also evaluated.

The present invention has a fundamental construction in which pulse-like heating is applied to a thin-film material having a high thermal conductivity such as a diamond thin film, and a response characteristic exhibited at this time is measured as a change in temperature of the thin film, to thereby evaluate the thermal influence of the material to be measured which is in contact with the thin-film material on the thin-film material in accordance with the response characteristic.

Then, in the present invention, fundamentally, a sensor for measuring the thermal influence of the material to be measured and a sensor for measuring a temperature of the material to be measured and a temperature of the measuring environment both having the above-mentioned construction are used, and output from these two sensors are processed in accordance with a predetermined relational expression, to thereby obtain an output not depending on a temperature of the material to be measured and a temperature of the measuring environment.

As that output, there is, for example, a flow rate of fluid which flows in contact with the thin-film material. That is, in this case, there can be obtained a value corresponding to a flow rate value which does not depend on a temperature of fluid or a temperature of measuring environment. Here, one of the fundamental constructions of the present invention was treated in outline. However, there are a variety of forms and embodiments in accordance with the present invention as will be described later.

2. Description of the Related Art

As devices for measuring a flow rate (in general, called a flow sensor), there are known devices using a thermistor. The devices of this type utilize a phenomenon that a temperature on the thermistor portion is lowered by allowing the quantity of heat to be absorbed by fluid. In general, when the thermistor portion is in contact with fluid, the quantity of heat removed from the thermistor portion depends on the flow rate (or flow velocity). Therefore, there is a correlation between the output from the thermistor and the flow rate. Using this fact, the flow rate can be calculated in accordance with the output from the thermistor.

The flow rate is a product of a sectional area of fluid and a flow velocity, and for example, if fluid of a fluid velocity v flows into a circular pipe of an inner diameter r, the flow velocity is represented by $v\pi r^2$. Hence, if the sectional area of fluid is known, the flow rate and the flow velocity can be obtained simultaneously.

In general, the thermistor is directed to a semiconductor having a large negative temperature coefficient. However, the thermistor originally means a thermally sensitive resistor, and in particular is not defined by plus or minus of the temperature coefficient or material. Therefore, such material as platinum having a positive temperature coefficient may be called a thermistor.

An element using a material whose resistance is changed in accordance with a temperature such as the thermistor is generally called a resistance bulb, a temperature sensing element, a temperature detector or a resistance thermometer. Also, a material whose resistance is changed in accordance with a temperature is called a material having a thermistor function. Hereinafter, a material whose resistance is changed in accordance with a temperature is called a resistance bulb.

As a method of measuring a flow rate, apart from the construction using the thermistor as described above, there is a method in which a resistant heating element which has been heated by joule heat is immersed into fluid in order to utilize the phenomenon that the quantity of heat is absorbed from the resistant heating element depending upon the flow rate. In this method, the flow rate can be calculated by measuring an electric current flowing into the resistant heating element.

Further, there is a method in which the quantity of heat is absorbed by fluid from the heating element which is in contact with the fluid, and the quantity of heat carried with the fluid is measured by a resistance bulb (for example, a platinum sensor) disposed separately, to thus calculate the flow rate.

In these methods, for the purpose of gaining a high sensitivity, it is effective to increase the quantity of heat absorbed by the fluid. Further, in order to heighten a response speed, it is necessary to make the heat capacity of the resistance bulb portion as small as possible.

The flow rate measuring devices (flow sensors) using the above-described construction cause a problem that a range of the measurable flow rate is narrowed, that is, a dynamic range is narrowed. In concrete, in such measuring devices, the flow rate cannot be measured with accuracy except for the ranges of 20 to 300 sccm, 200 to 2000 sccm.

It is considered that these problems are mainly caused by the following reasons.

(1) Since the resistance bulb is thermally put in a extremely unstable state, a heat response linear property is lowered so that it cannot follow a thermal change over a wide range.

(2) In relation to the above item (1), in particular, a heating method is difficult, and effective heating cannot be made over a wide range of the flow rate.

(3) When the thermal capacity of the resistance bulb is reduced in order to increase a response speed, a large quantity of heat cannot be dealt with.

The above item (1) is caused by the fact that it is difficult to effectively absorb the quantity of heat from the resistance bulb by the fluid over a wide range of the flow rate while the quantity of heat is effectively supplied to the resistance bulb at the same time.

Further, since the resistance bulb sensitively detects not only the flow rate but also a change in a temperature of environment (for example, a change in a temperature of fluid), there arises a problem when using the resistance bulb under the environment where a temperature is changed. There have been proposed a variety of methods for solving these problems, however, under existing circumstances, when actually using the resistance bulb, the measurement of the flow rate greatly disperses depending upon an environment of the measurement and a temperature of fluid.

The inventors have prepared a device for measuring the flow rate as shown in FIG. 1. In FIG. 1, reference numeral 13 denotes a polycrystalline diamond thin-film having a thickness of 5 $\mu$m which has been synthesized in gas phase by using the magnetic field microwave CVD technique; 12, a resistance bulb of platinum having a thickness of 1 $\mu$m which has been formed by the spattering technique; 11, a resistant heating element of platinum having a thickness of 0.1 $\mu$m which has been formed by the spattering technique, likewise; 10 and 15, electrodes thereof; 17, a gold wire for bonding; and 18, a substrate made of Teflon for holding the diamond thin film 13. The resistance bulb 12 is different from heating element 11 only in resistance. The resistant value of the resistant bulb 12 is approximately 1 K$\Omega$ whereas that of heating element 11 is approximately 100 $\Omega$.

In the flow rate measuring device shown in FIG. 1, the diamond thin film 13 is held by the Teflon substrate 18 in such a manner that it is thermally insulated from elements other than the fluid. Thus, since the thin-film material is held so as to be thermally insulated therefrom, it is structured so that heat does not flow out from the thin-film material to elements except for fluid, as a result of which the thermal interaction between fluid and the thin-film material can be evaluated with accuracy.

Further, a fluid 19 is structured so as to flow in contact with a surface opposite to that at which the resistance bulb 12 and the heating element 11 are formed. In more detail, the flow rate measuring device shown in FIG. 1 is fitted into a part of a plastic pipe into which the fluid flows, and one surface (a surface on which a circuit is formed) of the diamond thin film faces on an external portion of the pipe and the other surface thereof faces on an interior portion of the pipe. Then, the pipe is in contact with the substrate 18 made of Teflon so that the diamond thin film is not directly in contact with the pipe.

The system by which the measurement has been actually executed is shown in FIG. 2. In FIG. 2, reference numeral 22 denotes a flow rate measuring device, an outline of which is shown in FIG. 1. In the system shown in FIG. 2, a pulse-like voltage is applied from an amplifier 21 to the heating element 11, and the heating element 11 pulsedly heats the diamond thin film 13 (refer to FIG. 1). The pulse-like heating is executed for a very short time, for example, 0.18 seconds. The diamond thin film 13 is heated by pulse-like heating in a very short time.

The transient response characteristic of the diamond thin film 13 in accordance with the pulse-like heating due to the heating element 11 is detected by the resistance bulb 12 as a change in temperature of the diamond thin film 13. A given bias voltage is applied to the resistance bulb 12 so that a change in the temperature of the diamond thin film 13 is outputted as a change in a value of current flowing in the resistance bulb.

An output signal of the resistance bulb 12 is converted into a voltage signal by means of an I/V amplifier 24, and is then converted into a digital signal by means of an A/D converter 25. Further, an output signal from the A/D converter 25 is processed by means of a CPU 28 by a predetermined calculating manner, whereby a measured value is outputted from a D/A converter 27. The amplifier 21 and the A/D converter 25 are controlled by a timing pulse generator 23. The predetermined calculating manner will be described later on the description of a basic sensor operating method.

As a result of measuring the flow rate of nitrogen gas by use of the flow rate measuring device shown in FIG. 1 and the system using that measuring device shown in FIG. 2, the following experimental facts have been obtained.

(1) The response characteristic of the diamond thin film to instant heating (pulse-like heating) depends upon the flow rate of the fluid which flows so as to be in contact with the diamond thin film. When the response characteristic is quantitatively evaluated, then the flow rate (or flow velocity) can be measured.

(2) However, the response characteristic mentioned on the above item (1) is changed even depending upon a temperature of the fluid. That is, even though the flow rate is identical, if a temperature of the fluid or a temperature of environment is different, a corresponding response characteristic is also made different. This means that it is difficult to distinguish a change in the flow rate from a change in temperature of the fluid or the measurement environment.

The photograph related to the above experimental fact (1) is shown in FIG. 3. FIG. 3 is a photograph in which an output signal of the I/V amplifier 24 is displayed in an oscilloscope. In FIG. 3, the axis of ordinate represents a temperature of the diamond thin film whereas the axis of abscissa represents a time. In FIG. 3, there is shown such a state that the diamond thin film is rapidly cooled by nitrogen gas after it is rapidly heated. This corresponds to the transient response characteristic of the diamond thin film to the pulse-like heating. The heating time is 0.18 seconds and the gas temperature is constant (room temperature). Also, the bias voltage applied to the resistant bulb 12 is $V_{cc}=0.3$ V.

Two curves shown in FIG. 3 exhibit the response characteristics corresponding to a different flow rate, respectively. This means that the response characteristics of the diamond thin film to the pulse-like heating are different in accordance with a difference of the flow rate. In FIG. 3, a larger waveform represents a case where the flow rate is small, and a smaller waveform represents a case where the flow rate is large.

This is understood as a mechanism stated below. That is, when the flow rate is small, since the quantity of heat absorbed from the diamond thin film is small, the diamond thin film is rapidly largely heated when pulse-like heating, and then is slowly cooled. Therefore, the response waveform becomes large. On the other hand, when the flow rate is large, since the quantity of heat absorbed from the diamond thin film is large, the diamond thin film is not heated to a so high temperature and also rapidly cooled after completion of heating. Therefore, the response waveform becomes small.

The operation in the CPU 28 is executed by calculating an area of the waveform as shown in FIG. 3 within a predetermined period of time. In concrete, the operation is fundamentally identical with the operation of the sensor to be described later with reference to an embodiment of the invention.

The relationship between the quantity of nitrogen gas (S1, liter/min) of a constant temperature obtained in the above manner and its measurement tolerance is shown in FIG. 4. The tolerance exhibits the reliability of the measured data and is a parameter exhibiting a difference between an accurate value and a measured value. In flow rate measurement shown in FIG. 4, the measurement was made in such a manner that the Reynolds number of the fluid which is in contact with the flow rate measuring device is smaller than 2,000. The reason is to restrain an increase of the tolerance due to any influence of turbulent flow.

From FIG. 4, in the case where the temperature of the fluid is constant, when the flow rate is 2 to 42 (liters/min), the measurement within 3% (±1.5%) can be executed. If the tolerance of 50% is permitted, the measurement from 0.05 (liters/min)(50 sccm) can be made, and the flow rate can be measured over three figures or more.

Subsequently, the experimental fact regarding that a change in the temperature of fluid and a change in the flow rate of fluid cannot be distinguished from each other as stated on the above item (2) will be described below.

Symbol A of FIG. 5 represents an output signal of the D/A converter 27 in the case where a sensor portion 22 (having a construction shown in FIG. 1) shown in FIG. 2 is disposed within a thermostatic chamber and a temperature of fluid (air) is changed from 10° to 35° C. under the condition where the flow rate is 0.

In this case, as shown by A of FIG. 5, if the temperature of the fluid (in this case, it can be regarded as a temperature of fluid) is changed, even though the flow rate is not changed (in this case, the flow rate is constant, that is zero), the output from the measuring system shown in FIG. 2 is changed.

From the experimental data shown in FIG. 5, it is concluded that, in the case of using the measuring system as shown in FIG. 2, when the temperature of fluid and a value of the flow rate are changed simultaneously, it is impossible to decide which of the temperature of the fluid and the value of the flow rate is changed in principal.

SUMMARY OF THE INVENTION

An object of the present invention is to provide a measuring device and method which can prevent a change of the measured value of the flow rate due to a change in a temperature of the fluid or measurement environment and can obtain an output signal depending on only the flow rate (or flow velocity).

Another object of the present invention is to provide a measuring device for evaluating a thermal interaction between the thin-film material and the material to be measured, which can obtain a measured value not depending on a temperature of material to be measured and the measuring environment.

(As to the Principal of the Invention)

As described above, when a sensor shown in FIG. 1 is brought in contact with fluid using the system shown in FIG. 2, the output from the D/A converter depends on two variables of the flow rate and the temperature of the fluid or the measuring environment.

Here, let us consider two sensors. These sensors has a construction as shown in FIG. 1. Also, the operating method of the sensors is to measure the response characteristic of the diamond thin film to pulse-like heating as described above. In this case, the output from the sensor corresponds to an area of the response waveform shown in FIG. 3.

First, as one sensor, let us consider use of a temperature measuring sensor which detects the temperature of the fluid without contacting the flow of fluid. That is, this temperature sensor is arranged in such a manner that the flow rate of the fluid becomes 0 even though the sensor is contact with the fluid. In this case, the output from the temperature measuring sensor does not depend on the flow rate, but depends on the temperature of the fluid and/or the temperature of the measurement environment.

Also, as the other sensor, let us consider a sensor which is directly in contact with the flow of fluid for obtaining an output which depends on the flow rate of fluid and the temperature of the fluid and the temperature of the fluid and/or the measuring environment (hereinafter, referred to as "temperature of fluid"). Hereinafter, this sensor is called a fluid measuring sensor.

Here, let us consider that these two sensors has the same characteristics electrically and thermally. In this case, the output from the temperature measuring sensor depends on the temperature of the fluid. On the other hand, the output from the fluid measuring sensor depends on the flow rate and the temperature of the fluid. Hence, it is understood that a difference between the output from these two sensors corresponds to the flow rate.

These matters can be considered as follows:

(1) It can be considered that an output from the fluid measuring sensor is equal to a sum of an output depending on the temperature and an output depending on the flow rate.

(2) The output depending on the temperature of (1) is equal to the output from the temperature sensor.

(3) Hence, it can be considered that a difference between the output from the fluid measuring sensor and the output from the temperature measuring sensor does not depend on the temperature but corresponds to the flow rate.

Thus, the temperature measuring sensor and the fluid measuring sensor having the same characteristic are prepared to obtain a difference between the output from both the sensors, thereby being capable of executing the measurement of the flow rate with accuracy regardless of the temperature of the fluid or of the measuring environment.

The above-mentioned fundamental operational principle will be described using actually measured data. What is shown in FIG. 6 represents a relationship between the output (reference: abscissa axis (arbitrary value)) of the temperature measuring sensor and the output (sensor output: ordinate axis (arbitrary value) from the fluid measuring sensor.

Here, the temperature measuring sensor and the fluid measuring sensor have the same structure. In concrete, they have the structure as shown in FIG. 1.

The temperature measuring sensor, as shown by reference numeral 802 in FIG. 8, is arranged in such a manner that it is not directly immersed in a flow 90 of fluid, but is in contact with fluid flowing from a slit 95 to a space 98. With such a construction, since the flow rate of fluid in contact with the temperature measuring sensor 802 can be regarded as 0, the temperature measuring sensor 802 does not detect the flow rate. That is, since it can be regarded as a state where the fluid with which the temperature measuring sensor 802 is in contact hardly flows, it is said that the output from the temperature measuring sensor 802 is hardly influenced by the flow rate.

The flow measuring sensor are arranged so as to be directly in contact with the flow 90 of fluid, as shown by reference numeral 803 in FIG. 8, to detect the flow rate. However, the flow measuring sensor also detects the temperature of fluid at the same time.

FIG. 6 shows a relationship between an output (abscissa axis) from the temperature measuring sensor (REFERENCE sensor) and an output (ordinate axis) from the fluid measuring sensor (SENSOR) at the time where a temperature within a thermostatic chamber is changed from −20° to 60° C. in a state where the flow rate is 0. Here, the fluid is air. The output from the sensor called here is an output which has been operated and processed by a manner to be described later.

In a state where the flow rate is 0, the fluid measuring sensor functions as a temperature measuring sensor. Therefore, if the two sensors have the same characteristic, plotted dots shown in FIG. 6 form a linear straight line having an inclination of 1 and an intercept of 0. However, in fact, there are dispersion of the characteristics for the respective sensors and offset voltage in the output from an analog circuit, a straight line plotted as shown in FIG. 6 has an inclination slightly smaller than 1 and an intercept which is not 0.

A graph shown in FIG. 6 represents a case where the flow rate is 0. Here, let us consider a case where fluid flows. In this case, as the output from the temperature measuring sensor (REFERENCE) does not depend on the flow of fluid, the values on the abscissa axis in FIG. 6 are not changed. On the other hand, the output from the fluid measuring sensor is a sum of a value corresponding to the temperature of fluid and a value corresponding to the flow rate, the value on the ordinate axis is changed only by a value corresponding to the flow rate. Also, in this case, it can be considered that the flow rate is not changed in accordance with the temperature. Hence, the respective plots shown in FIG. 6 are moved in the ordinate axial direction by a predetermined value corresponding to the flow rate.

In the case where fluid flows as its result, the straight line shown in FIG. 6 is moved substantially in parallel. Then, in this case, the amount of movement of the straight line corresponds to the flow rate.

As the flow rate is increased as shown in FIG. 3, the response waveform is decreased. Therefore, the output from the sensor is reduced. Hence, the parallel movement of the straight line shown in FIG. 6 when the flow rate is not 0 (zero) is toward a minus direction of the ordinate axis in FIG. 6.

As described above, in the case where the temperature measuring sensor and the fluid measuring sensor have the same characteristic, a relationship between the output from the temperature measuring sensor and the output from the fluid measuring sensor is represented by a linear function. That is, the relationship between the output R (corresponding to the abscissa axis in FIG. 6) from the temperature measuring sensor and the output S (corresponding to the ordinate axis in FIG. 6) from the fluid measuring sensor is represented by the following expression (1).

$$S = AR + B - F \qquad (1)$$

In expression (1), A and B are constants. If the temperature measuring sensor and the fluid measuring sensor have the same characteristic, then A=1. Also, if the temperature measuring sensor and the fluid measuring sensor have the same characteristic and the offset voltage of the circuit is 0, then B=0. F is a value corresponding to the flow rate which is not influenced by the temperature of the measuring environment or the fluid.

Since data exhibited in FIG. 6 is a case of no-flow state (flow rate=0), naturally F=0. In data shown in FIG. 6, because of problems such as dispersion of the characteristic of the respective sensors or the offset voltage of the circuit, A=1 and B=0 are not satisfied.

What is required for flow rate measurement is to obtain a value corresponding to the flow rate without dependency on the temperature. In expression (1), A and B can be previously obtained at a calibrating stage. For example, the values of A and B can be readily obtained from FIG. 6.

Accordingly, if the output R from the temperature measuring sensor and the output S from the fluid measuring sensor are ascertained, an F corresponding to the flow rate not depending on the temperature of the fluid is obtained from expression (1).

Expression (1) is satisfied by a case where the temperature measuring sensor and the fluid measuring sensor have the nearly same characteristic, or a case where they have the substantially same characteristic. In general, the output R from the temperature measuring sensor and the output S from the fluid measuring sensor are represented by a relationship exhibited by the following expression (2).

$$F = f(R) - S \qquad (2)$$

In expression (2), f(R) represents the function of R. The form of this function is determined by the difference in the characteristic between the temperature measuring sensor and the fluid measuring sensor. If both the sensors have the substantially same characteristic, then f(R)=AR+B (A and B are constant), which is identical with expression (1).

If using expression (2), even though the characteristic is different between the temperature measuring sensor and the fluid measuring sensor, the value of the flow rate or flow velocity which does not depend on the temperature of fluid or measuring environment can be obtained.

The form of the function f(R) can be known at the calibrating stage in advance. That is, the form of the function f(R) can be known by measuring data as shown in FIG. 6 at a predetermined flow rate.

Hereinafter, the primary construction of the present invention will be described. Hereinafter, an example in which a diamond thin film is utilized as a thin film material of a sensor portion is shown, and as other materials, there can be used single crystalline silicon, polycrystalline silicon, hydrocarbon silicon, aluminum nitride, boron nitride, or other materials of high thermal conductivity (materials having the thermal conductivity of at least monocrystal silicon (148 $Wm^{-1}K^{-1}$, 300K) or more. Of course, in the case of using the diamond thin film, the most remarkable effect can be obtained.

As a material to be measured, fluid is first applied. However, a solid material may be applied as a material to be measured. For example, in the case where the material to be measured is fluid, the measurement of the flow rate of fluid or flow velocity, or discrimination of the kind of fluid can be executed. This utilizes the fact that the way of the change (in other words, the response characteristic) in temperature of the thin-film material by being heated thereof is different in accordance with the flow rate or kind of the fluid which flows in contact with the thin-film material. Also, the impurity within fluid can be detected by using the phenomenon that the thermal conductivity and the specific heat of fluid differs with an impurity contained in the fluid.

Also, when the material to be measured is solid, the way of a change in temperature of the thin-film material by being heated thereof is different, that is, its response characteristic differs in accordance with a difference of the thermal conductivity of the solid, a difference of the specific heat, or a difference of the thermal capacity. Using this phenomenon, the kind of the solid material can be discriminated or a difference of volume of the solid material can be measured.

One primary construction of the present invention is to compare a first response characteristic determined in accordance with primary variables α and β with a second response characteristic determined in accordance with the variable a to obtain an output corresponding to the variable β.

Here, there can be shown an example where α is a temperature of fluid and β is a flow rate of fluid. Also, there can be shown an example where α is a temperature of fluid and β is a variable corresponding to the kind of fluid or a difference of its physical property.

When β is a variable corresponding to the kind or physical property of fluid, the kind of fluid or a difference in a value of the physical property can be known from the value of β. This can be used for a gas detecting sensor.

The response characteristic means a response characteristic of the thin-film material having a high thermal conductivity to pulse-like heating. The primary variables a and β means that the primary factors are α and β.

To generally say the above construction, it is to compare the first response characteristic determined in accordance with variables $\alpha_1, \alpha_2 \ldots \alpha_{n+1}$ with the second response characteristic determined in accordance with variables $\alpha_1, \alpha_2 \ldots \alpha_n$ to obtain an output corresponding to the variable $\alpha_{n+1}$, where n is a natural number expressed by 1, 2, 3 . . .

For example, in the measurement of the flow rate, when the flow rate and the temperature of fluid are in question, that is, when attention is given to these two factors as primary factors, if the flow rate is the variable $\alpha_1$ and the temperature of fluid is the variable $\beta_1$, this construction coincides with the above-mentioned construction which is to compare a first response characteristic determined in accordance with primary variables α and β with a second response characteristic determined in accordance with the variable α to obtain an output corresponding to the variable β.

However, factors such as the kind of fluid or the concentration or density of the impurity other than the flow rate and the temperature of fluid contribute to the response characteristic as shown in FIG. 3. The above-mentioned construction is characterized in that those factors are expressed by the variables $\alpha_1, \alpha_2 \ldots \alpha_{n+1}$, and an output related to one factor $\alpha_{n+1}$ among those factors is obtained.

For example, when the construction as shown in FIG. 9 which will be described at a second embodiment of the invention is applied, a sensor denoted by reference numeral 802 exhibits the response characteristic depending on the temperature of fluid corresponding to the variable $\alpha_1$ and the various physical properties of fluid corresponding to the variables $\alpha_2$ to $\alpha_n$. Here, the various physical properties means variables exhibiting the thermal properties of material such as the thermal conductivity of fluid, the coefficient of kinematic viscosity, the density of fluid or the specific heat of fluid.

On the other hand, a sensor denoted by reference numeral 803 exhibits the response characteristic depending on the variable $\alpha_{n+1}$ corresponding to the flow rate of fluid which flows in a pipe 91 in addition to the above variables $\alpha_1$ to $\alpha_n$.

The respective response characteristics are evaluated quantitatively to compare the above two response characteristics with each other, thereby being capable of obtaining an output corresponding to the variable $\alpha_{n+1}$ which corresponds to the flow rate. The output represents the flow rate and is not influenced by factors of the variables $\alpha_1$ to $\alpha_n$.

One of the primary constructions of the present invention is characterized in that there are provided a plurality of sensors having means for pulsedly heating a thin-film material having a high thermal conductivity, for example, a diamond thin film and means for measuring a response characteristic of the thin-film material to the pulse-like heating due to the heating means, in which at least one of these sensors is a sensor for measuring the temperature of fluid and at least another one is a fluid measuring sensor arranged in contact with fluid, and a means for processing the output from the temperature measuring sensor and the output from the fluid measuring sensor on the basis of a predetermined functional relationship.

In the above construction, if the temperature measuring sensor and the fluid measuring sensor fundamentally have the same construction, their structure is simple and their operation is also simple. The temperature measuring sensor is to obtain an output depending on the temperature of fluid or measuring environment. For example, in the case where the system as shown in FIG. 2 is immersed in the fluid which does not flow, its output corresponds to the temperature of fluid as shown in FIG. 5(A). In this case, the sensor denoted by reference numeral 22 in FIG. 2 functions as a temperature measuring sensor.

When the sensor shown in FIG. 1 is used as the temperature measuring sensor, it is not immersed in the flow 90 of fluid, as indicated by reference numeral 802 in FIG. 8.

The fluid measuring sensor must be directly immersed in the flow 90 of fluid as indicated by reference numeral 803 in FIG. 8. With such a construction, an output depending on the flow rate of fluid can be obtained. However, this output simultaneously depends even on the temperature of fluid or environment.

The predetermined functional relationship in the above-mentioned construction means a relationship between the output R from the temperature measuring sensor as represented by expression 1 or 2 and the output S from the fluid measuring sensor. The output from both the sensors are processed in accordance with this relational expression, thereby being capable of obtaining the measured value of the flow rate which does not depend on the temperature of fluid or measuring environment.

The output from the sensor stated here is obtained by performing fundamental operation which will be described later. Simply speaking, the output is a value obtained by integrating an area of the waveform representative of the response characteristic of the thin-film material as shown in FIG. 3 (refer to the basic sensor operating method which will be described later).

In the above construction, as a means of pulsedly heating the thin-film material, it is general to use a resistant heating element provided in direct contact with the thin-film material. It is also considered that the thin-film material is indirectly heated, joule-heated by electrically energizing the thin-film material per se, or heated by light, laser beam or microwaves.

The measurement of the response characteristic of the thin-film material is executed by measuring the temperature of the thin-film material. For example, in the construction as shown in FIGS. 1 and 2, the response characteristic of the diamond thin film 13 to pulse-like heating from the heating element 11 is measured by the resistance bulb 12 as a change in temperature of the diamond thin film 13. As a result of this measurement, the output from the resistance bulb 12 is changed as shown in FIG. 3. The output change represents the response characteristic of the diamond thin film 13 to pulse-like heating.

As a means for measuring the temperature of the thin-film material, it is general to use a resistance bulb (for example, platinum) disposed in contact with the thin-film material. Also, there can be used a structure in which a semiconductor is used as a thin film, and a semiconductor layer having one conductive type is formed on a surface of the semiconductor by the ion injecting technique or the like to thereby forming a layer which functions as the resistance bulb in the thin-film material or on a surface thereof. Also, the thin-film material per se can be used as the resistance bulb. For example, if a diamond thin film which is subjected to the p-type by adding B (boron) at a gas-phase synthesizing stage is used as the thin-film material, the thin film per se can be used as the resistance bulb. Also, a technique for detecting a heat ray generated by the thin-film material (for example, thermography) can be also used as a means for measuring the temperature of the thin-film material.

It is important that the means for measuring the temperature of the thin-film material detects only the temperature of the thin-film material. For example, let us consider that a diamond thin film is used as the thin-film material and mounted on a silicon substrate in such a manner that the resistance bulb is disposed between the diamond thin film and the silicon substrate. In this case, the resistance bulb measures both temperatures of the diamond thin film and the silicon substrate at the same time. The thermal conductivity of the silicon substrate is 148 ($Wm^{-1}K^{-1}$, 300K) and its value is very small in comparison with the thermal conductivity about 1000 ($Wm^{-1}K^{-1}$, 300K) of the diamond thin film, or more. Therefore, the response characteristic to pulse-like heating which is detected by the resistance bulb is dull whereby an excellent characteristic cannot be obtained.

Also, in the case where a resistance heating element which is provided in direct contact with the thin-film material is used as the means for heating the thin-film material, and a resistance bulb is used as the means for measuring the temperature of the thin-film material, there is required that the heating element and the resistance bulb are thermally coupled to each other only through the thin-film material.

This is because, when the resistance bulb detects the quantity of heat from the heating element regardless of a response of the thin-film material, elements other than the response characteristic of the thin-film material are contained in the response characteristic of the thin-film material.

Further, there is required that the thin-film material is prevented from being in contact with material other than the material to be measured to the utmost and held in a thermally levitated state. This is also because, at the time of pulse-like heating, the response characteristic of material other than the thin-film material is prevented from influencing a measured result. For example, in the case where the diamond thin film is used as the thin-film material and the material to be measured is of fluid, a temperature of which is kept constant, it is ascertained that the more the thermal insulating property when holding the diamond thin film is enhanced, the more the response characteristic of the diamond thin film to pulse-like heating depends on the flow rate of the fluid.

That is, in the case of measuring the flow rate, the quantity of heat escaped from the thin-film material is classified into the following three forms.

(1) The quantity of heat escaped from the surface of the thin-film material to fluid.

(2) The quantity of heat escaped to a substrate which holds the thin-film material.

(3) The quantity of heat escaped from lead wires connected to the heating element provided in contact with the thin-film material or the resistance bulb.

It is important to reduce the influence of the factors (2) and (3) among them as large as possible.

The temperature of the material to be measured and/or measurement environment means the following three cases.

(1) A case of making both the temperatures of the material to be measured and the measurement environment as an issue.

(2) A case of making the temperature of the material to be measured as an issue.

(3) A case of making the temperature of the measurement environment as an issue.

In general, since the temperature of the material to be measured is changed by the change in the temperature of the measurement environment, it is considered normal to execute the measurement under the condition (1).

However, there is considered a case where the temperature of the measurement environment means the temperature of the fluid as it is, and in this case, the temperature measuring sensor makes it unnecessary to measure the temperature of fluid, and measures the temperature of the measurement environment. That is, in this case, it is not required to hold the temperature measuring sensor in the sate as indicated by reference numeral 802 in FIG. 8, and it may be structured so that the temperature measuring sensor measures the temperature of the atmosphere external to the pipe 91.

One of the primary constructions of the present invention is characterized in that there are provided a plurality of sensors including a thin-film material, means for pulsedly heating the thin-film material and means for measuring the response characteristic of the thin-film material in accordance with pulse-like heating, in which at least one sensor among the plurality of sensors has a function for measuring the temperature of a reference fluid and/or the temperature of the measurement environment, and at least another sensor among the plurality of sensors is arranged in contact with the fluid to be measured, and a means for processing the output from the temperature measuring sensor and the output from the fluid measuring sensor on the basis of a predetermined functional relationship.

The above-described construction can be used for the measurement such as the discrimination of the kind of fluid; the detection of a specified fluid; the measurement or discrimination of impurities contained in fluid (for example, the measurement of humidity in air); the measurement of a mixing ratio of different fluids; the measurement of the density of fluid; the measurement of the thermal conductivity of fluid; and the measurement of the specific heat of fluid. Also, it goes without saying that it can be used for the measurement of the flow rate.

In the above construction, it is necessary that the reference fluid which is in contact with the respective sensors, more particularly, the flow rate of the fluid to be measured is always kept constant, preferably the flow rate is 0 (zero). This is because an influence of the flow of fluid on the measured value is prevented. Also, it is necessary that the reference fluid and the fluid to be measured are maintained at the same temperature.

Hereinafter, a case of discriminating the kind of fluid will be described. If the kind of fluid is different, then the value of the physical property such as the thermal conductivity or the specific heat is also naturally different. Hence, when executing the measurement by using the measuring system as shown in FIG. 2 in a state of a specific flow rate (for example, the flow rate is 0), it is sure that the response characteristic of the thin-film material as shown in FIG. 3 is different.

What contributes to a difference of the response characteristic is a value of the physical property related to the thermal property of fluid. For example, it is of the thermal conductivity, the specific heat, the density or the like.

Also, since the difference of the output as shown in FIG. 3 is influenced by the temperature of the fluid to be measured or the temperature of the measurement environment, it is necessary to remove such an influence. Hence, using the temperature measuring sensor for measuring the temperature of reference fluid and/or the temperature of the measurement environment as in the above construction, the output R from the temperature measuring sensor which is in contact with the reference fluid and the output S from the fluid measuring sensor which is in contact with the fluid to be measured are processed in accordance with a predetermined relational expression represented by expression 1 or 2. As a result, the output F corresponding to the physical property of the fluid to be measured can be obtained with no dependency on the temperature of the fluid or the measuring environment.

In this case, the value F calculated by operation based on this predetermined relationship becomes a different value depending on the kind of the fluid to be measured. Consequently, the kind of the fluid to be measured can be discriminated from the value of F.

The above-described measuring principle is applied to a case of the above-mentioned objects to be measured, likewise. For example, in the case where an object to be measured is the density of an impurity in fluid, the value F differs in accordance with the density of the impurity in the fluid to be measured, thereby being capable of knowing the density of the impurity. Also, when the density of fluid is different, the value F differs in accordance with a difference of the density, and utilizing this, the density of fluid can be measured.

In the above-mentioned construction, the reference fluid is necessary for giving the measured value of the fluid to be measured a relative meaning. For example, in the case of discriminating the kind of fluid, let us consider that nitrogen is used as a reference fluid. In this case, it is judged from the output whether or not the fluid to be measured has a different physical property in comparison with the nitrogen fluid.

BRIEF DESCRIPTION OF THE DRAWINGS

The present invention will be described in more detail with reference to the accompanying drawings, in which.

Figure 1:
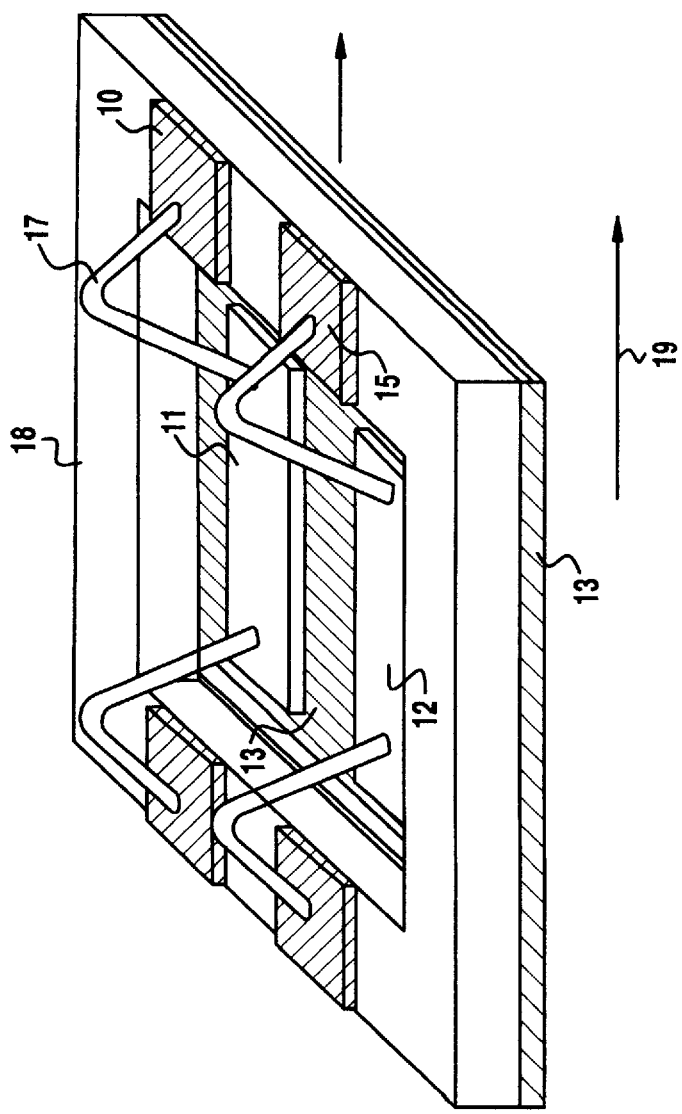
FIG. 1 is a schematic diagram showing the structure of a sensor in accordance with the present invention.
Figure 2:
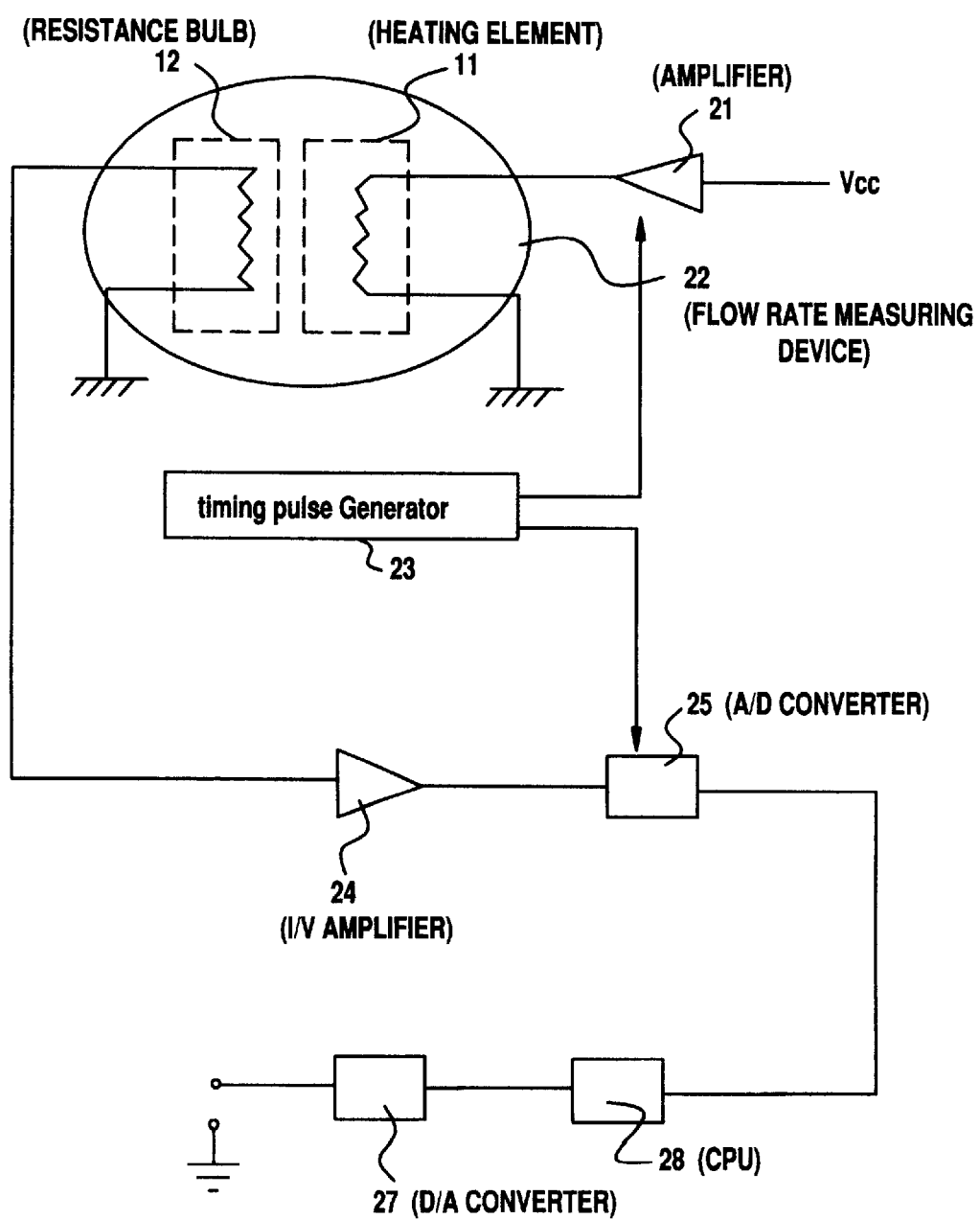
FIG. 2 is a diagram showing the structure of a flow rate measuring device.

DETAILED DESCRIPTION OF THE PREFERRED EMBODIMENTS (First Embodiment)

In a first embodiment, a method of manufacturing a sensor shown in FIG. 1 will be described. A sensor shown in FIG. 1 includes a heating element 11 formed of a platinum (Pt) thin film, a resistor 12 which functions as a resistance bulb and their electrodes 10 and 15 on a surface of a polycrystal diamond thin film 13 having an area of 4 mm×4 mm and a thickness of 5 $\mu$m.

Hereinafter, a process of manufacturing the sensor shown in FIG. 1 will be described. First, a silicon substrate having a diameter of 4 inches is prepared. Then, a surface of the silicon substrate is subjected to a flawing process due to diamond powders. A diamond thin film having a thickness of 5 $\mu$m is synthesized in gas phase on the flawed surface of the silicon substrate by the magnetic field microwave CVD technique. In the magnetic field microwave CVD technique, high-density plasma is formed by use of a strong magnetic field and the microwaves of 2.45 GHz to thereby perform the synthesis of the gas phase.

The film forming conditions are exhibited below.

Substrate temperature: 800° C.
Reactive pressure: 0.25 Torr
Microwave power: 4 KW
Reactive gas: $CH_3OH:H_2=1:4$
Film forming time: 10 hours
Film thickness: 5 $\mu$m The silicon substrate is put on a place having the magnetic field intensity of 875 gauss. The diamond thin film obtained under the above film forming conditions is of a polycrystal diamond thin film and has a structure that the crystal grows from the silicon substrate in a vertical direction.

The film forming technique is not limited by or to the above-described method, and other gas-phase techniques may be applied thereto. Also, a natural diamond or a high-pressure synthesized diamond may be used. Further, the diamond thin film may be doped with an impurity so as to control the thermal characteristic or the electrical characteristic. The crystal structure is not limited by or to a polycrystal, but a single-crystal diamond thin film may be used.

As the diamond thin film, it is preferable to provide a low content of the impurities and a thermal conductivity as high as possible. Also, the thickness of the diamond thin film is preferably made thin as far as the mechanical strength is permitted in view of the productivity.

The diamond thin film formed on the silicon substrate is peeled off from the silicon substrate, thereby being capable of obtaining a simple substance of the diamond thin film. The process is readily performed by mechanically peeling off the diamond thin film or by melting the silicon substrate with hydrofluoric acid or the like.

The diamond thin film thus obtained is cut into chips of a 4 mm square, and a platinum thin film having a thickness of 800 to 1000 Å is formed on the diamond thin film by the spattering technique. The spattering is performed by using a platinum target and accelerating air of spattering gas to the degree of 1 KeV. The sheet resistance of the platinum thin film formed on the diamond thin film is of a 100 $\Omega/\square$ or so.

Further, as shown in FIG. 1, a heating element 11 and a resistance bulb 12 are formed on the diamond thin film 13 by the patterning technique. In concrete, the areas of the heating element 11 and the resistance bulb 12 are adjusted so that the resistance of the heating element 11 is of a 100 $\Omega$ or so and the resistance of the resistance bulb 12 is of a 1 K$\Omega$ or so, as a result of which the heating element 11 and the resistance bulb 12 are distinguished. This distinction may be also made by changing the film thicknesses of the heating element 11 and the resistance bulb 12. Further, the diamond thin film 13 is held by a Teflon substrate 18 so that electrodes 10 and 15 are formed thereon and bonding is then made by a gold wire 17 of 10 $\mu$m$\Phi$. As a result, the sensor as shown in FIG. 1 is completed.

Since the resistance bulb 12 is sensitively reactive to temperature so that the resistance of the resistance bulb 12 is changed, it can be also called a layer having a thermistor function.

In the case of changing the number of the resistance bulbs, the number of the heating elements and a method of arranging the resistance bulbs and the heating elements, it may be based on the above-mentioned manufacturing process. Also, the size of the diamond thin film may be further decreased. In this case, it is expected that the consumed power is reduced and the sensitivity are improved.

The thermistor parameter of the resistance bulb 12 which is formed of a platinum thin film shown in FIG. 1 was about 200 ppm. This corresponds to a change of the resistance of 0.02% with respect to a change of temperature of 1° C. In general, since the thermistor parameter of the resistance bulb using platinum is of 100 to 3000 ppm, the resistance bulb of a still higher sensitivity can be obtained if the manufacturing conditions are qualified.

In the construction shown in FIG. 1, the thermal capacity of the resistance bulb 12 which is formed of the platinum thin film is 1 per several hundreds or less in comparison with the thermal capacity of the diamond thin film 13. Therefore, the thermal capacity of the resistance bulb can be almost ignored in comparison with the thermal capacity of the diamond thin film, and a change in temperature of the diamond thin film can be detected by the resistance bulb 12 at an extremely high speed and also with a high sensitivity. In the case where the thermal capacity of the resistance bulb cannot be ignored in comparison with the thermal capacity of the diamond thin film, the change in temperature of the diamond thin film cannot be detected with accuracy by influence of the change in temperature of the resistance bulb per se. In concrete, it is necessary that the thermal capacity of the diamond thin film is 100 times or more as large as the thermal capacity of the resistance bulb.

(Second Embodiment)

Figure 7:
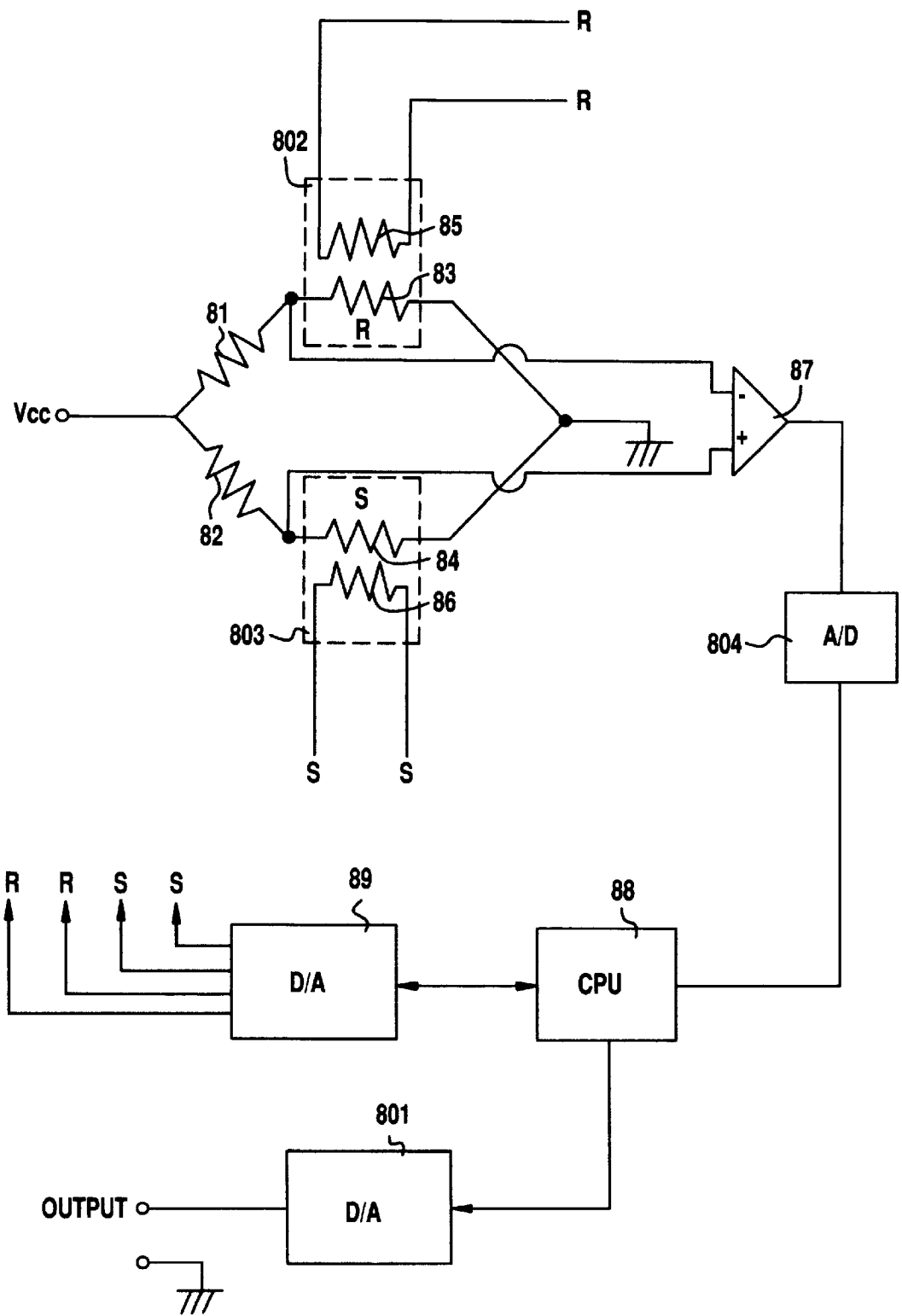
FIG. 7 is a diagram showing the structure of a measuring system in accordance with one embodiment of the present invention.
Figure 8:
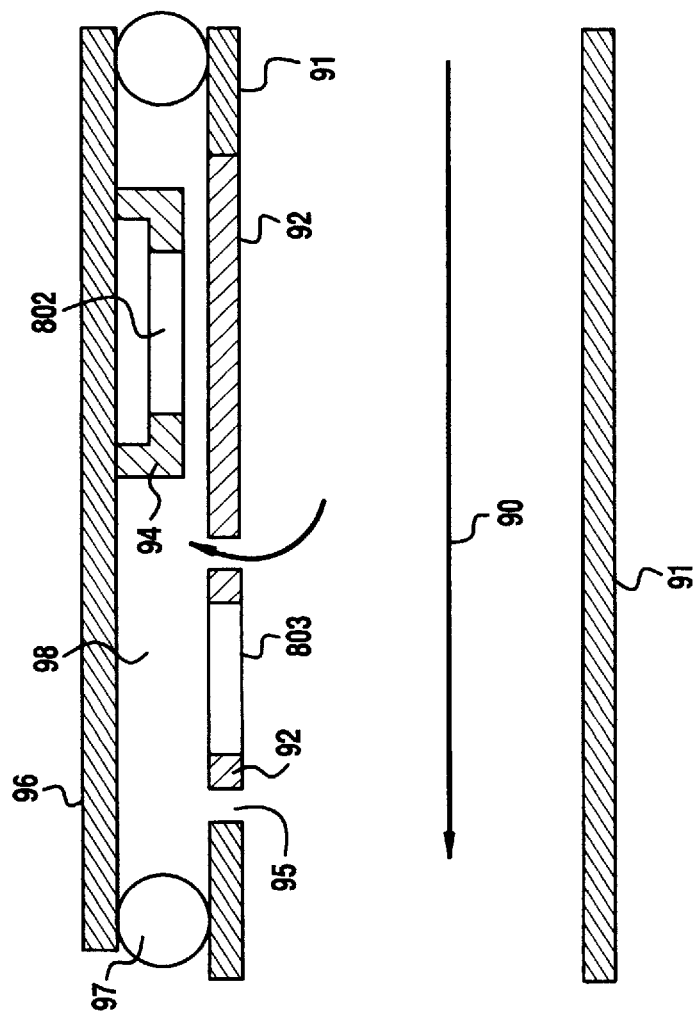
FIG. 8 is a diagram showing an arrangement state of the measuring sensor.
Figure 9:
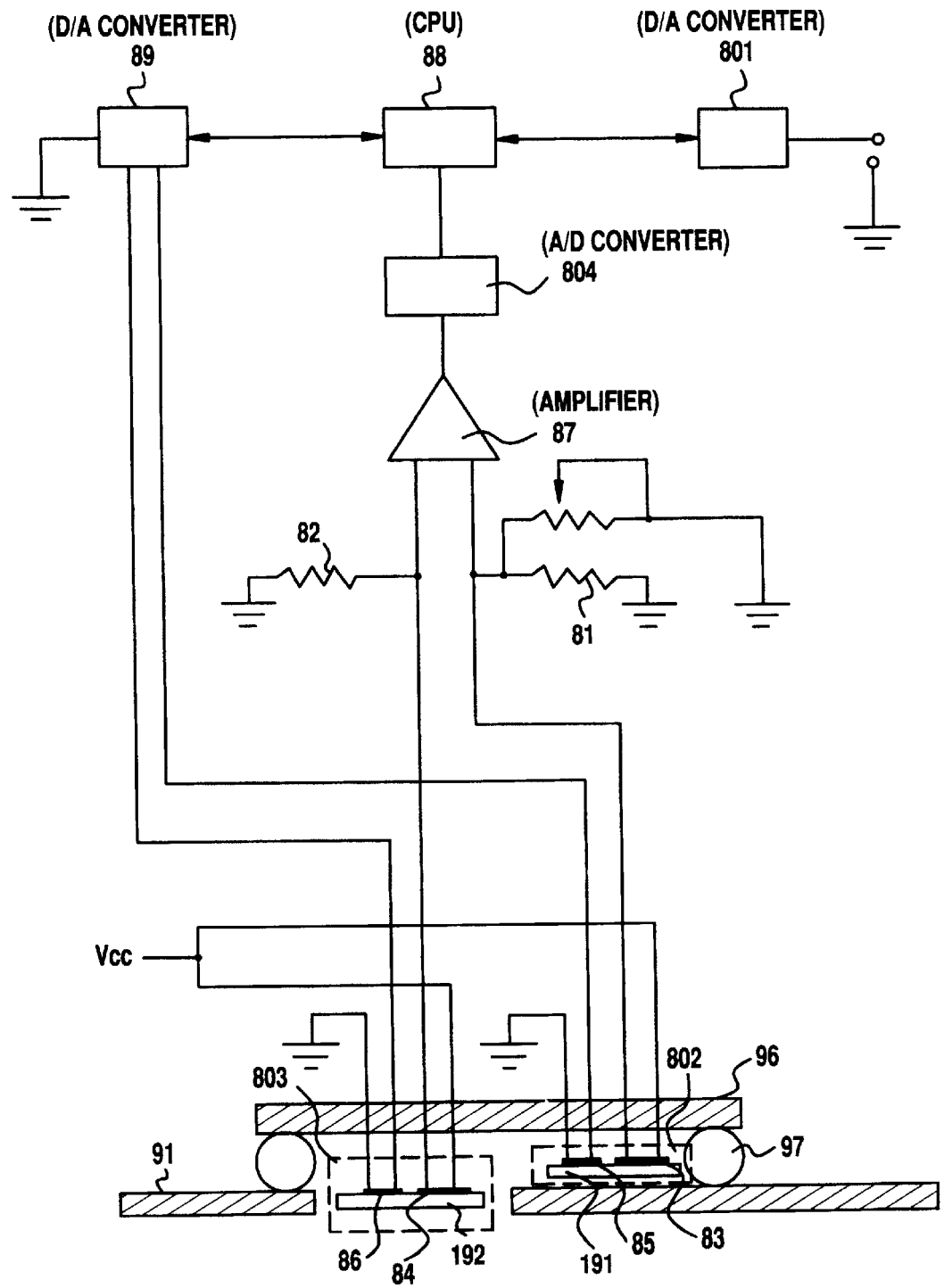
FIG. 9 is a diagram showing the structure of a measuring system in accordance with another embodiment of the present invention.

An outline of the construction in accordance with a second embodiment is shown in FIGS. 7 to 9. This embodiment shows an example in which the flow rate of fluid is measured. The primary factors are of the flow rate and the temperature of fluid. Consequently, the kind of fluid and its various physical properties are not considered. This embodiment can be used for a gas flow meter which is capable of measuring an accurate flow rate with no influence of the temperature of gas in the case where the kind of gas to be measured is known.

This embodiment of the invention has a construction embodying the fundamental construction stated below.

That is, the embodiment provides a measuring device which includes means for obtaining a first response characteristic in accordance with the flow rate of fluid and the temperature of fluid, means for obtaining a second response characteristic in accordance with the temperature of fluid, means for comparing the first response characteristic with the second response characteristic to calculate the flow rate of fluid; and means for detecting the response characteristic as a change in temperature of the thin-film material to pulse-like heating.

In the above fundamental construction, the means for obtaining the first response characteristic in accordance with the flow rate of fluid and the temperature of fluid corresponds to a fluid measuring sensor 803. Also, the assembly of the fluid measuring sensor 803, an amplifier 87, an A/D converter 804 and a CPU 88 can be called the above means.

Further, in the above fundamental construction, the means for obtaining the second response characteristic in accordance with the temperature of fluid corresponds to a temperature measuring sensor 802. Also, the assembly of the temperature measuring sensor 802, the amplifier 87, the A/D converter 804 and the CPU 88 can be called the above means.

Further, in the above fundamental construction, the means for comparing the first response characteristic with the second response characteristic to calculate the flow rate of fluid corresponds to the CPU 88.

Further, in the above fundamental construction, the means for detecting the response characteristic as a change in temperature of the thin-film material to pulse-like heating corresponds to resistance bulbs 83 and 84. Also, in addition to the resistance bulbs 83 and 84, the assembly of the amplifier 87, the A/D converter 804 and the CPU 88 can be called the above means.

Figure 10:
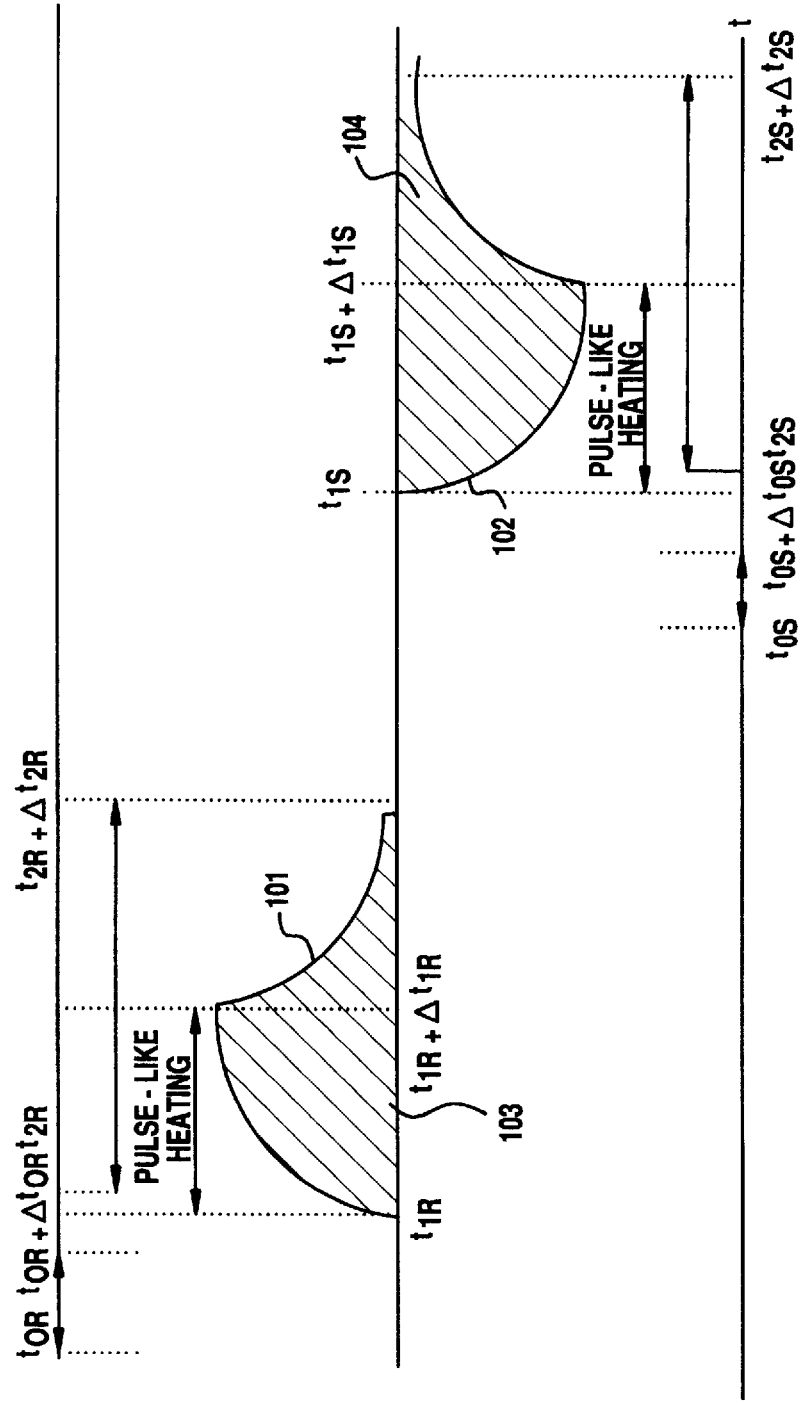
FIG. 10 is a graph representing a response waveform of a diamond thin film to pulse-like heating.

Hereinafter, the respective structural elements will be described. In FIGS. 7 to 9, FIG. 7 shows a block diagram of a measuring device, FIG. 8 shows an arranging state for sensors 802 and 803 with respect to a pipe 91, and FIG. 10 shows a wiring state. These figures show the same one in different views. In FIGS. 7 to 9, reference numerals 802 and 803 denote sensors having the construction shown in FIG. 1. In this embodiment, the respective sensors 802 and 803 have the same structure and size as well as the same characteristic.

The sensor 802 functions as a temperature measuring sensor for measuring the temperature of fluid. The sensor shown in FIG. 1 can be also utilized as the temperature measuring with the following reason.

As shown in FIGS. 8 and 9, if the sensor 802 is structured so as to be out of contact with the flow of fluid, the thermal influence on the sensor 802 is caused only by the temperature of the fluid and environment. Therefore, the sensor 802 can be used as a temperature sensor. In the temperature measuring sensor 802, reference numeral 85 denotes a heating element which functions to pulsedly heat the diamond thin film to thereby supply a predetermined quantity of heat to the film. Reference numeral 83 denotes a resistance bulb which functions to detect the response characteristic of the diamond thin film to pulse-like heating due to heating element 85 as a change in the temperature of the diamond thin film.

On the other hand, the sensor 803 functions as the flow rate measuring sensor with such an arrangement that the sensor 803 is in direct contact with the fluid. In the flow rate measuring sensor 803, reference numeral 86 denotes a heating element which functions to pulsedly heat the diamond thin film so as to supply a predetermined quantity of heat to the film. Reference numeral 84 denotes a resistance bulb which functions to detect the response characteristic of the diamond thin film which is pulsedly heated by the heating element 86 as a change in temperature of the diamond thin film.

These two sensors 802 and 803 constitute a bridge circuit by the aid of resistors 81 and 82. In the actual construction, as shown in FIG. 9, a variable resistor is connected in parallel to one resistor 81 to execute offset adjustment.

An output from the bridge circuit is inputted to an A/D converter 804 through an amplifier 87. An output from the A/D converter 804 is inputted to a CPU 88 to perform given operation. The CPU used in this embodiment includes a memory within one chip, and the memory stores therein the relational expression represented by expression (1). Then, in the CPU, the output F corresponding to the flow rate is calculated on the basis of the output R from the temperature measuring sensor 802 and the output S from the fluid measuring sensor 803.

An output from the D/A converter 801 is of an output representing the flow rate. On the other hand, the D/A converter 89 functions to apply pulsed voltage to the heating element 85 of the temperature measuring sensor 802 and the heating element 86 of the flow rate measuring sensor 803 at a predetermined timing.

FIGS. 8 and 9 show a state where the temperature measuring sensor 802 and the fluid measuring sensor 803 are actually arranged. In FIGS. 8 and 9, reference numeral 91 denotes a pipe in which fluid flows. Reference numeral 90 denotes a flow of fluid. The pipe 91 is made of appropriate material (in this case, plastic). A part of the pipe 91 is hollowed, and a Teflon substrate 92 is inserted in the hollowed part. It is important that the substrate 92 is made of material such as Teflon or epoxy resin which is thermally insulative in comparison with diamond.

As shown in FIG. 8, a part of the substrate 92 is also hollowed, and the flow rate measuring sensor 803 is inserted in the hollowed part. With such a structure, the diamond thin film can be held in a thermally insulative state so that an accuracy in measurement can be enhanced.

In FIG. 8, the details of the temperature measuring sensor 802 and the flow rate measuring sensor 803 are not shown. However, as shown in FIG. 9, the heating elements 85, 86 and the resistance bulbs 83, 84 are formed on the diamond thin films 191 and 192.

Also, a plate 96 made of plastic is disposed on the pipe 91 through an O-ring 97, and a space 98 is shielded from the exterior. On the other hand, slits or openings 95 are formed in the substrate 92 so that a part of the fluid 90 flows into a space which is defined by the plate 96 and the O-ring 97. The space 98 may communicate with the exterior, however, in the case where the pressure of fluid is high, the fluid may leak from that portion to the exterior. Therefore, it is preferable that the space 98 communicates with only the interior of the pipe 91.

Also, as shown in FIG. 8, the temperature measuring sensor 802 is held in a thermally levitated state by the aid of the substrate 94 made of a thermally insulator such as teflon or epoxy resin. When the construction shown in FIG. 8 is applied, the flow velocity of the fluid in contact with the temperature sensor 802 is nearly zero or kept constant. Therefore, it can be considered that the output from the temperature measuring sensor 802 almost depends on the temperature of fluid.

Also, it is ascertained that, even though the direction in which the fluid 90 flows is opposite in the figure, a measured value is not adversely affected.

(As To Fundamental Sensor Operating Method)

Figure 4:
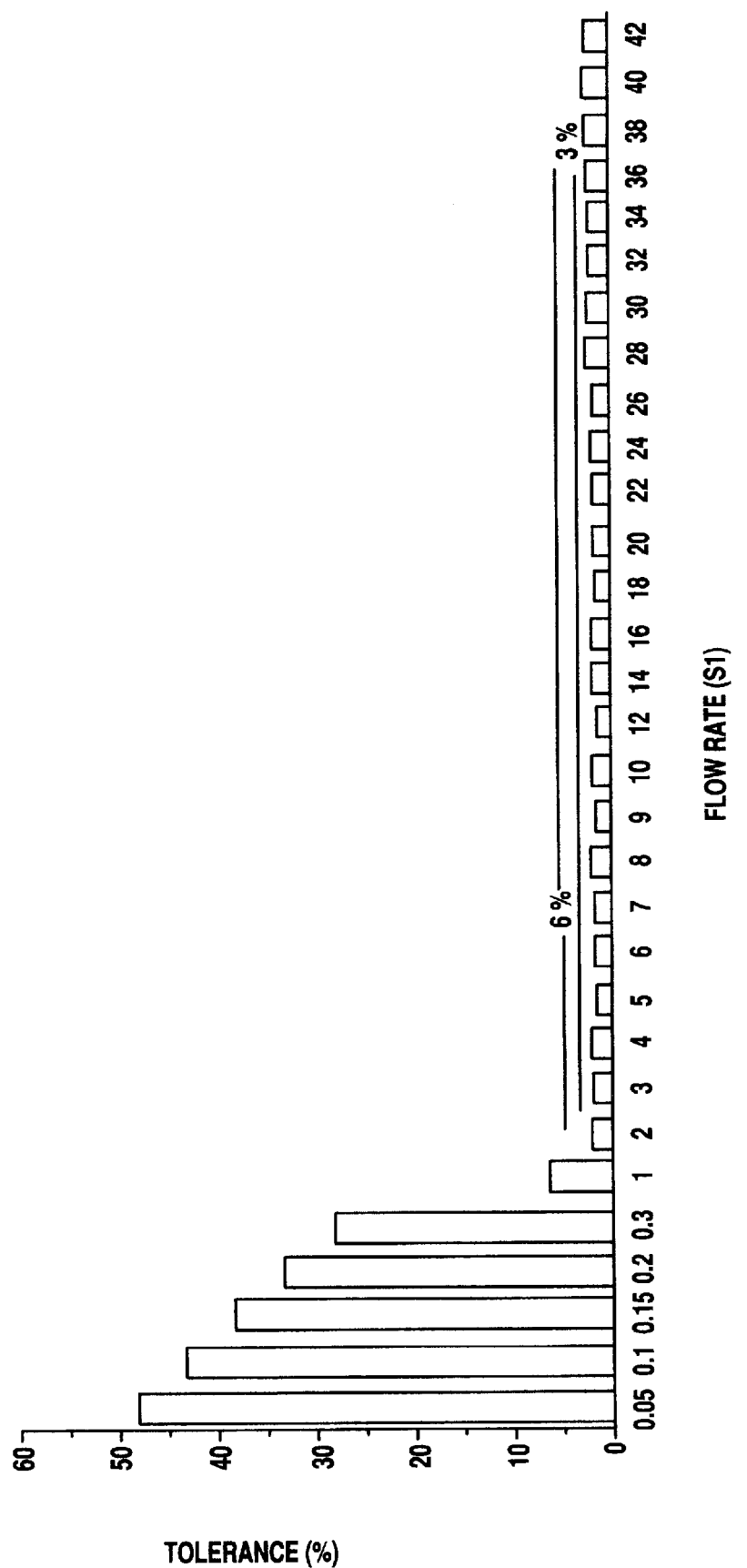
FIG. 4 is a graph representing a relationship between a flow rate and a tolerance in flow rate measurement.

Hereinafter, the fundamental sensor operating method will be described with an example of the temperature measuring sensor 802 shown in FIGS. 7 and 9. The operation is common to the respective sensors. Also, the sensors has the construction shown in FIG. 1. The output from the sensor is obtained by the operating method stated below. Also, the method of measuring the flow rate whose result is shown in FIG. 4 is conducted in accordance with the operating method stated below.

First, FIG. 10 will be described. FIG. 10 shows a change in an output from the amplifier 87 in the system shown in FIGS. 7 and 9, and there are shown an output change 101 from the resistance bulb 83 in the temperature measuring sensor 802, and an output change 102 from the resistance bulb 84 in the fluid measuring sensor 803.

Hereinafter, the concrete operating procedure will be described.

(First Operation)

In $t_{OR}$ to $t_{OR}+\Delta t_{OR}$, the output from the D/A converter 804 is integrated in the CPU 88. This calculation is executed in accordance with the following calculating expression (3). Also, the integrated value is $S_{OR}$.

$$S_{OR} = \int_{t_{OR}}^{t_{OR}+\Delta t_{OR}} fdt \qquad (3)$$

A reference point in the measurement of temperature by the temperature measuring sensor 802 can be decided with the first operation. This operation is very important in order to obtain an accurate evaluation without drift.

(Second Operation)

An electric power is applied to the heating element 85 at a given voltage for a period of $\Delta t_{1R}$ to pulsedly heat the diamond thin film constituting the temperature measuring sensor 802.

A change in temperature of the diamond thin film heated by the above second operation is outputted as a change in resistance value of the resistance bulb 83. For example, when the output from the amplifier 87 is observed through an oscilloscope, a waveform represented by reference numeral 101 in FIG. 10 is observed. This exhibits a state that the diamond thin film is rapidly heated by pulse-like heating and then cooled.

(Third Operation)

The output from the A/D converter 804 is integrated in accordance with the following expression (4) during $t_{2R}$ to $t_{2R}+\Delta t_{2R}$. The integrating operation is executed by the CPU 88. Also, its integrated value is $S_{2R}$, and $t_{1R}<t_{2R}$. This is because noises appear in the output if $t_{1R}=t_{2R}$.

$$S_{2R} = \int_{t_{2R}}^{t_{2R}+\Delta t_{2R}} fdt \qquad (4)$$

(Fourth Operation)

The CPU 88 operates a difference between $S_{OR}$ and $S_{2R}$. This operation is equivalent to calculation of an area indicated by an oblique line 103 in FIG. 11, and with this operation, only the response characteristic of the diamond thin film which is not influenced by the drift component can be obtained.

In concrete, the above fourth operation is conducted by executing the operation represented by $(S_{OR}/\Delta t_{OR})-(S_{2R}/\Delta t_{2R})$. $(\Delta t_{2R}/\Delta t_{OR})S_{OR}-S_{2R}$, or $S_{OR}-(\Delta t_{OR}/\Delta t_{2R})S_{2R}$. Since it is necessary to obtain an absolute value of a difference between $S_{OR}$ and $S_{2R}$, the order of subtraction may be reverse. The result of this operation is an output from the sensor.

The area of the oblique line portion 103 of the waveform in FIG. 10 obtained by the above fourth operation reflects the thermal influence on the diamond thin film, and for example, it is changed depending on the temperature or flow rate of the fluid which is in contact with the diamond thin film.

Here, it is assumed that the diamond thin film constituting the sensor 802 is in contact with the flow of the fluid having a constant temperature. Then, the output obtained by the above fourth operation represents the flow rate of the fluid. What is obtained in this case is data represented by FIG. 4. This is an example where the various conditions in obtaining data shown in FIG. 4 are $\Delta t_{0R}$=0.1 sec., $\Delta t_{1R}$=0.18 sec., $\Delta t_{2R}$=0.36 sec., voltage applied to the heating element is 3.2 V, and the bias voltage Vcc applied to the resistance bulb 83 is 0.3 V.

As shown by the sensor 802 in FIG. 8 or 9, in the case where the sensor is arranged so as not to be immersed in the flow 90 of fluid, when the above operation is executed, the output from the sensor 802 obtained as a result of that operation depends on a temperature of fluid or environment. In other words, the output corresponding to the temperature of fluid or environment can be obtained (refer to FIG. 5(A)).

In the above operating procedure, the method of evaluating the response characteristic of the diamond thin film by obtaining the difference between $S_{0R}$ and $S_{2R}$ is important. With such an operation, no drift component appears in the output, and an accurate measurement with no time-elapsed change can be executed.

(Calibration of Sensor in Advance)

For the measurement of the flow rate, before operating the sensor, it is necessary to previously calibrate the sensor. This calibrating operation is conducted as stated below. It is necessary that the work is conducted at least after assembling the construction shown in FIGS. 7 to 9. Hereinafter, an example where the flow rate is measured will be described.

(1) A construction shown in FIG. 8 is placed in an environment where fluid to be measured is filled and the temperature of the fluid can be changed with accuracy. For example, when the flow rate of nitrogen gas is to be measured, the sensor is placed in a thermostatic chamber which is filled with nitrogen gas. The flow rate is zero (a constant flow rate) under this state.

(2) In this state, the temperature measuring sensor 802 is operated by the method explained in the above-described basic operation. An output from the temperature measuring sensor at this time corresponds to an area 103 of the waveform 101 in FIG. 10. In this embodiment, as various conditions, for example, Vcc=0.3 V, a voltage to be applied to the heating element is 3.2 V, $\Delta t_{0R}$=0.1 second, $\Delta t_{1R}$=0.18 seconds, and $\Delta t_{2R}$=0.36 seconds.

(3) The fluid measuring sensor 803 is executed under the condition where the output obtained by the above operation (2) is kept constant. That is, the fluid measuring sensor 803 is operated under the condition where the temperature of the fluid is kept constant. The operating method of the fluid measuring sensor 803 also complies with the above-mentioned operation. That is, the two sensors 802 and 803 are operated in the entirely same driving method and driving condition. The output 803 of the fluid measuring sensor at this time corresponds to an area 104 of a waveform 102 in FIG. 10.

As a result of this operation, the output from the temperature measuring sensor and the output from the fluid measuring sensor are obtained by a pair. This means that one of plots shown in FIG. 6 is determined.

(4) The above operation is repeated every given temperature while changing the temperature of an atmosphere within a thermostatic chamber within an range of required temperature.

Figure 6:
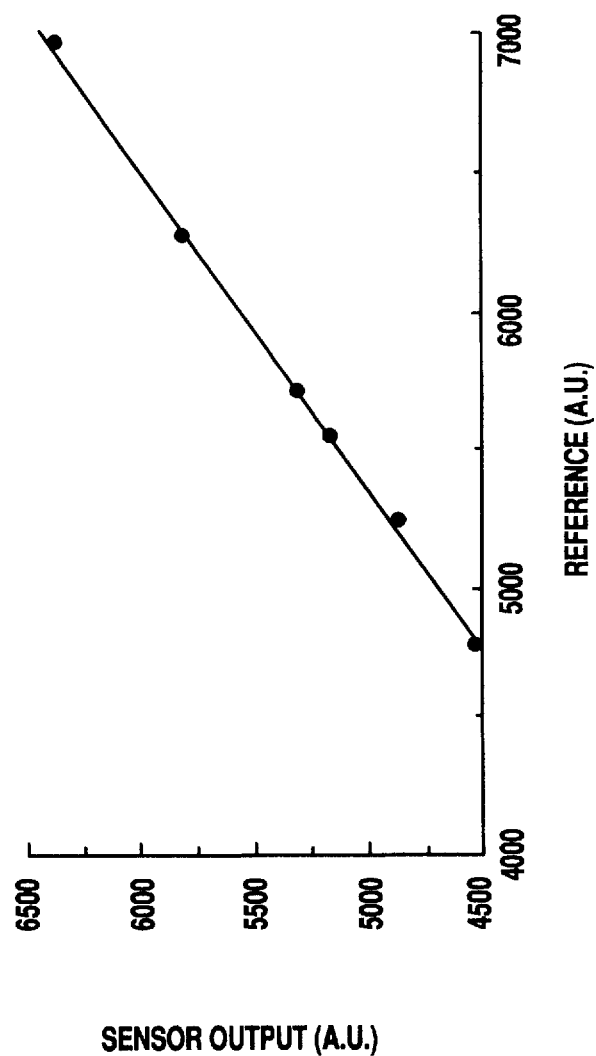
FIG. 6 is a graph representing a relationship between an output from a temperature measuring sensor and an output from a flow rate measuring sensor.

For example, if −10° to 50° C. are within an operating range, a temperature is changed at −10°, 0°, 10°, 20°, 30°, 40° and 50° C., and the function shown in FIG. 6 is prepared with the coordinates of the output (abscissa axis) of the temperature measuring sensor 802 and the output (ordinate axis) of the fluid measuring sensor 803 at that time.

As described above, if the temperature measuring sensor 802 and the fluid measuring sensor 803 have the same characteristic, a function obtained in the above operation becomes a linear function having an inclination of 1 and an intercept of 0 under an ideal condition. However, in fact, the inclination is not 1 and also the intercept is not 0 because of the factors such as dispersion of the characteristic of the respective sensor and the offset voltage of the circuit.

That is, what is actually obtained is a function shown in expression 7. Here, R is an output from the temperature measuring sensor, $S_0$ is an output from the fluid measuring sensor, and A and B are constants. Also, A and B can be obtained as concrete numeral values. In the following expression (7), $S_0$ represents an output from the fluid measuring sensor in the case where the flow rate is 0.

$$S_0 = AR + B \tag{7}$$

When the temperature measuring sensor and the flow rate measuring sensor have the same size and structure so as to have the same characteristic, the function obtained by the above operation becomes a nearly complete linear function as shown in expression (7). Hence, in this case, it is practical if only two plotted dots are taken.

With this operation, the constants A and B in expression (1) or the function f(R) in expression (2) can be obtained.

(5) The function obtained by the above operation is stored in a memory within the CPU 88, or the operating method based on this function is programmed in the CPU 88.

With the above operation, the calibration is completed. It is unnecessary that the function obtained in the calibration shown in FIG. 6 is calculated under the condition where the flow rate is 0. Also, the above mentioned method can be used even when the temperature measuring sensor and the fluid measuring sensor have different constructions or characteristics. In this case, the function f(R) of expression (2) can be obtained.

Also, it is necessary to previously obtain a relationship between the output from the D/A converter 801 and the flow rate of the fluid to be measured. This relationship may be stored in another memory although not shown in FIG. 8.

(Operation at the Time of Measuring the Flow Rate)

Hereinafter, the concrete operating method in the actual measurement of the flow rate will be described. In the measurement of the flow rate, it is necessary that the above-mentioned calibrating operation is completed in advance.

Fundamentally, a construction is made in accordance with an operating procedure stated below.

(1) The temperature measuring sensor 802 is operated to obtain a measured value in accordance with the temperature of fluid.

(2) The fluid measuring sensor 803 is operated to obtain a measured value depending on the temperature and flow rate of fluid.

(3) A predetermined operation is executed in the CPU 88 on the basis of the function represented by expressions (1) or (2) which has been obtained in advance.

Hereinafter, a concrete operating procedure will be described. The following description is given with reference to FIG. 10. FIG. 10 represents a change in the output from the amplifier denoted by reference numeral 87 in FIGS. 7 and 9 when observing the output through an oscilloscope.

Figure 11:
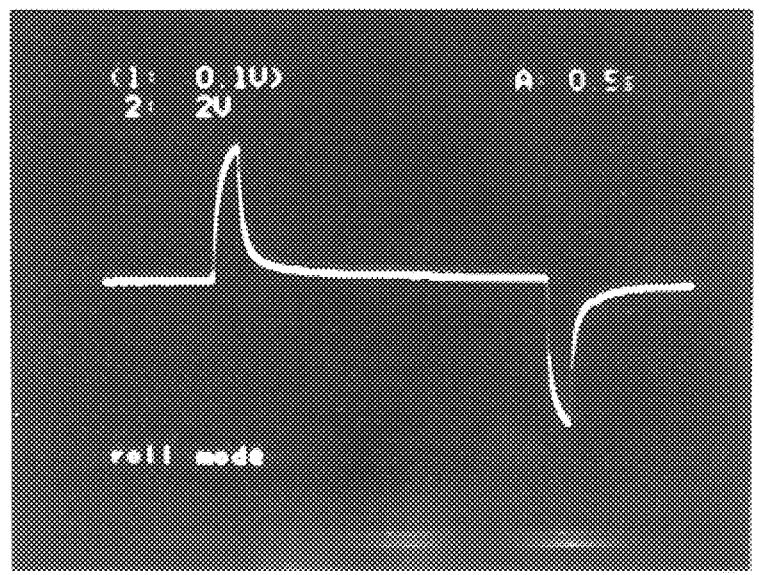
FIG. 11 is a diagram showing a photograph of an oscilloscope display.

FIG. 10 shows that the waveform denoted by reference numeral 101 is outputted by the amplifier 87 in accordance with a change in the resistant value of the resistance bulb 83 in the temperature measuring sensor 802, and subsequently the waveform denoted by reference numeral 102 is outputted by the amplifier 87 in accordance with a change in the resistant value of the resistance bulb 84 in the fluid measuring sensor 803. FIG. 11 shows a photograph of the actual display in an oscilloscope in correspondence with FIG. 10.

(First Operation)

In $t_{0R}$ to $t_{0R}+\Delta t_{0R}$, the output f of the D/A converter 804 is integrated in the CPU 88. This calculation is executed by expression (3). The integrated value is $S_{3R}$. Here, $\Delta t_{0R}=0.1$ seconds and Vcc=0.3 V.

$$S_{0R} = \int_{t_{0R}}^{t_{0R} + \Delta t_{0R}} f dt \tag{3}$$

With the first operation, a reference point at the time of measuring the temperature by the temperature measuring sensor 802 can be decided. This operation is extremely important for obtaining an accurate evaluation with no drift.

(Second Operation)

An electric power is applied to the heating element 85 at a constant voltage of 3.2 V for a period of time of $\Delta t_{1R}=0.18$ seconds to thereby pulsedly heat the diamond thin film constituting the temperature measuring sensor 802.

A change in temperature of the diamond thin film heated by the first operation is outputted as a change of the resistant value of the resistance bulb 83. For example, when the output from the amplifier 87 is observed by an oscilloscope, the waveform 101 in FIG. 10 is observed. This exhibits that the diamond thin film is rapidly heated by pulse-like heating and then cooled. According to the calculation, the heating temperature for the diamond thin film is about 20K.

(Third Operation)

The output from the resistance bulb 83 is integrated in $t_{2R}$ to $t_{2R}+\Delta t_{2R}$. The integrating operation is executed by the CPU 88 in accordance with the following expression (4). The integrated value is $S_{2R}$. Here, $\Delta t_{2R}=0.36$ seconds and $t_{1R}<t_{2R}$. This is because, if $t_{1R}=t_{2R}$, noises appear in the output.

$$S_{2R} = \int_{t_{2R}}^{t_{2R} + \Delta t_{2R}} f dt \tag{4}$$

(Fourth Operation)

In the CPU 88, a difference between $S_{0R}$ and $S_{2R}$ is calculated. This operation is equivalent to obtaining of the area indicated by the oblique line 103 in FIG. 11. With this operation, only the response characteristic of the diamond thin film not depending on the drift component can be obtained.

In concrete, this operation is executed by $(S_{0R}/\Delta t_{0R})-(S_{2R}/\Delta t_{2R})$, $(\Delta t_{2R}/\Delta t_{0R})S_{0R}-S_{2R}$, or $S_{0R}-(\Delta t_{0R}/\Delta t_{2R})S_{2R}$. Since what is necessary is an absolute value of a difference between $S_{0R}$ and $S_{2R}$, the order of subtraction may be reverse to the above order.

In this way, the output R depending not on the flow rate but only on the temperature of the fluid is obtained from the temperature measuring sensor 802. The above sequential operation is executed for four seconds.

(Fifth Operation)

Then, the fluid measuring sensor is operated. First, in the fluid sensor 803, the output from the resistance bulb 84 is integrated in $t_{0S}$ to $t_{0S}+\Delta t_{0S}$. The operation is executed by calculation represented by the following expression (5) in the CPU 88. Here, $\Delta t_{0S}=0.1$ seconds and $V_{cc}=0.3$ V.

$$S_{0S} = \int_{t_{0S}}^{t_{0S} + \Delta t_{0S}} f dt \tag{5}$$

The calculated result of expression (5) is $S_{0S}$. The fifth operation is executed in order to decide the reference point of the measuring operation in the fluid measuring sensor 803.

(Sixth Operation)

An electric power is applied to the heating element 86 of the fluid measuring sensor 803 at a constant voltage of b 3.2V for a period of time of $\Delta t_{1R}=0.18$ seconds to thereby pulsedly heat the diamond thin film constituting the fluid measuring sensor 803.

A change in temperature of the diamond thin film occurs in accordance with the sixth operation, and this is measured as a change in output from the resistance bulb 84. At this time, when the output from the amplifier 87 is monitored by the oscilloscope, the waveform 102 in FIG. 10 is observed. This waveform represents the response characteristic of the diamond thin film constituting the fluid measuring sensor 803 to pulse-like heating from the heating element 86.

(Seventh Operation)

The output from the A/D converter 804 is calculated in accordance with expression (6) between $t_{2S}$ and $t_{2S}+\Delta t_{2S}$. The calculated result of expression (6) is $S_{2S}$. In this embodiment, $\Delta t_{2R}=\Delta t_{2S}=0.36$ seconds, and their measuring time is also the same, however, they may not be identical with each other.

$$S_{2S} = \int_{t_{2S}}^{t_{2S} + \Delta t_{2S}} f dt \tag{6}$$

In the above expression (6), $t_{1S}<t_{2S}$. This is because, if $t_{1S}=t_{2S}$, then noises are contained in the output from the resistance bulb 84, to thereby lower accuracy in measurement.

(Eighth Operation)

A difference between $S_{0S}$ and $S_{2S}$ is calculated. In concrete, the calculation is conducted by $(S_{0S}/\Delta t_{0S})-(S_{2S}/\Delta t_{2S})$. $(\Delta t_{2S}/\Delta t_{3S})S_{0S}-S_{2S}$, or $S_{0S}-(\Delta t_{0S}/\Delta t_{2S})S_{1S}$. Since an absolute value of a difference between $S_{0S}$ and $S_{1S}$ is necessary, the order of subtraction may be reverse.

With the eighth operation, a value S corresponding to the area of an oblique part denoted by reference numeral 104 in FIG. 10 is obtained. The value S depends on the temperature of fluid and the temperature of environment. The fifth to eighth operations are also executed for four seconds.

(Ninth Operation)

Using the output R (output from the temperature measuring sensor 802) resulting from the fourth operation and the output S (output from the fluid measuring sensor 803) resulting from the eighth operation, the operation is executed in accordance with the following calculating expression (1) in the CPU 88.

$$S = AR + B - F \quad (1)$$

Here, since the constants A and B are obtained at a previously executed calibrating stage, the value of F can be decided. The F does not depend on the temperature of fluid, but depends only on the flow rate or flow velocity. Then, the output corresponding to the flow rate is obtained by the D/A converter 801.

In this embodiment, since a period of time during which the respective sensors operate is 4 seconds, a period of time required for one flow rate measurement becomes 8 seconds. In other words, the flow rate is measured at a rate of once per 8 seconds. The operating time can be further shortened. In concrete, it can be set to 2 seconds or less. In this case, it is required that a period of time for pulse-like heating ($\Delta t_{1R}$ and $\Delta t_{1S}$) be set to 100 ms or less.

Figure 5:
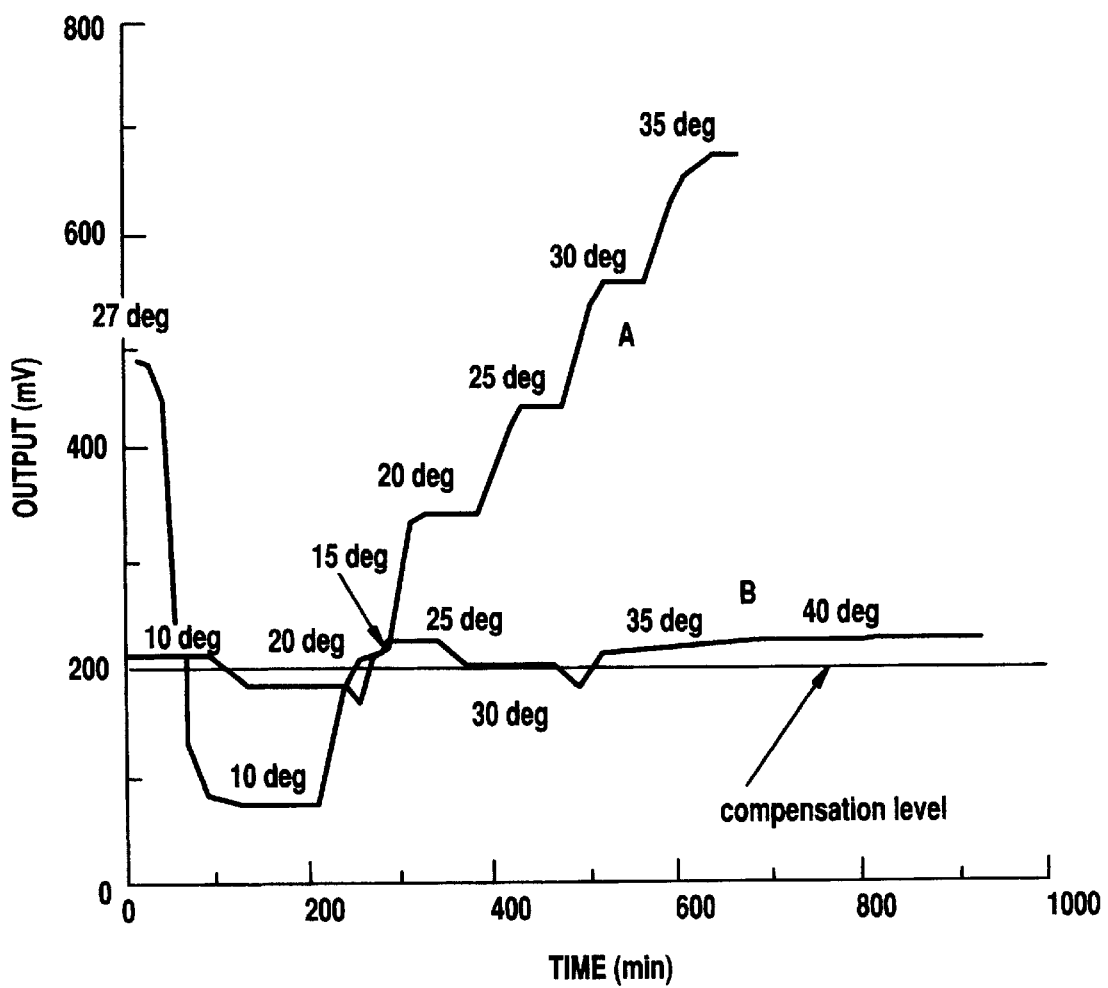
FIG. 5 is a graph representing a time-elapsed change of an output with respect to a change of temperature.

Data obtained by executing the measurement in accordance with the above operation is indicated by a line B in FIG. 5. The line B in FIG. 5 represents the time-elapsed change of the output from the D/A converter 801 in the case where a sensor having a structure shown in FIGS. 7 to 9 is placed in a thermostatic chamber which is filled with air and temperature is changed from 10° C. to 40° C.

In this case, it is considered that the flow rate is zero and kept constant, and the temperature of environment is the same as that of the fluid. Therefore, it is understood from data shown by the line B in FIG. 5 that an output reflecting a value of the flow rate (here, the flow rate is 0) is obtained without depending on a change in temperature of the fluid.

In accordance with the line B of FIG. 5, the drift caused by the change of temperature is about 30 mV or less at maximum, and this corresponds to the flow rate slightly less than about 20 sccm. The characteristic (the relationship between the flow rate and tolerance) of the flow rate measuring sensor in this embodiment is nearly identical with that of FIG. 4. An accuracy in measurement is slightly lowered by influence of the above drift component due to the change of temperature at the time of 1 slm (liter/minute).

When actually measuring the flow rate, a concrete value of the flow rate can be obtained by referring the output from the D/A converter 801 to a relationship between the value of the flow rate previously obtained and the output from the D/A converter 801.

As described above, in accordance with this embodiment, the flow rate sensor can be obtained which can conduct the measurement without any influence of temperature at 50 to 50000 sccm.

In this embodiment, the temperature measuring sensor 802 and the fluid measuring sensor 803 have the same structure and the same characteristic. Also, the heating time and the output operating time ($\Delta t_{2R}$ or $\Delta t_{2S}$) are the same between both the sensors. However, they may be set to different values, respectively. Also, the values of the respective parameters may be set to values timely required.

Further, when the temperature of fluid is controlled by the temperature of environment, without the structure shown in FIG. 8, it may be structured so that the temperature measuring sensor measures the temperature of environment. For example, in the structure shown in FIG. 8, the temperature measuring sensor is placed outside of the pipe, thereby being capable of providing a structure in which the temperature of the measurement environment is measured. Naturally, in this case, it must be devised so that the temperature measuring sensor is not directly immersed in the flow of fluid.

Also, even if the temperature of the fluid to be measured is not changed, there is a case where a drift of the output occurs in accordance with a change in temperature of the measurement environment. This is because a change in the resistant value of a resistor constituting the bridge denoted by reference numerals 81 and 82 in FIG. 7 or a drift of the amplifier are generated by changing the temperature of the measurement environment.

For solving this problem, it is constituted so as to measure both of the temperature of the fluid to be measured and the temperature of the measurement environment, and a correction term corresponding to a change in temperature of the measurement environment may be inserted in expression 1 or 2.

Also, a plurality of temperature measuring sensors and a plurality of fluid measuring sensors may be provided to average the output of the respective sensors.

(Third Embodiment)

In the second embodiment, the thermal influence of fluid on the temperature measuring sensor 802 is the temperature of fluid (here, making an issue of only the temperature of fluid), and the thermal influence received from fluid by the fluid measuring sensor 803 is the temperature of fluid and the flow rate of fluid.

In this embodiment, on the assumption that the construction shown in the second embodiment is used, a case where the density of the impurity in fluid which flows is changed and also the temperature of fluid is changed will be described. That is, in this case, the thermal influence on the respective sensors includes what is caused by the density of the impurity in the fluid.

Under these circumstances, there is a case of measuring the flow rate of air, whose temperature has been adjusted, that flows in piping or ducts in an air-conditioning equipment for a housing, a building or a public institution.

In the above air-conditioning equipment, the temperature of flowing air is different in accordance with the weather or seasons. Also, the humidity of flowing air is largely different in accordance with the weather or seasons.

Under these circumstances, when only the flow rate of air which flows in the wiring or duct is to be measured, it is necessary to obtain an output corresponding to only the flow rate without any influence of the temperature or humidity of air flowing in the wiring or duct.

In the construction of the second embodiment shown in FIGS. 7 to 9, the temperature measuring sensor is in contact with fluid but out of contact with the flow 90 of fluid, as shown in FIG. 8. Also, the fluid measuring sensor 803 is in contact with the flow 90 of fluid. Hence, in this case, a difference of the thermal influence on the two sensors is caused by only the flow 90 of fluid.

Therefore, even when measuring the flow rate of air in the above air-conditioning equipment, an output only depending on the flow of air, that is, an output depending on the flow rate can be obtained by executing the operating method of the second embodiment in the ideal circumstance. This output is directed to an output from the D/A converter 801.

The ideal circumstance is a case where the sensors 802 and 801 have the same characteristic, and A=1 and B=0 in expression (1). However, in fact, A is not 1 and B is not 0. Consequently, in this case, a correction term must be added in expression (1).

As a method except for adding the correction term, the following method can be applied. That is, at a state where the respective sensors are previously calibrated, an operating method is determined so as to satisfy expression (1) as much as possible in the case of A=1 and B=0, thereby being capable of realizing a circumstance close to the above ideal circumstance. For example, with the construction shown in FIGS. 7 to 9, in the measurement where the flow rate is 0, the calibration may be made so that the output from the sensor 802 and the output from the sensor 803 are identical with each other. Such a calibration is readily realized by changing program for the operation executed by the CPU 88.

The calibration is executed in a case of changing the temperature and in a case of changing the humidity, and it is necessary to satisfy a predetermined allowable range with respect to a change of both the variables within a measuring range. This is because expression (1) of A=1 and B=0 is not always completely satisfied with respect to the change of both the variables.

In the circumstance where the condition of A=1 and B=0 in expression (1) is roughly realized, the measurement of the flow rate of air in the above air-conditioning equipment corresponds to a case where, in the construction of comparing a first response characteristic determined in accordance with variables $\alpha_1, \alpha_2 \ldots \alpha_{n+1}$ with a second response characteristic determined in accordance with variables $\alpha_1, \alpha_2 \ldots \alpha_3$ to obtain an output corresponding to the variable $\alpha_{n+1}$ where n is a natural number represented by 1, 2, 3 . . . , n=2, $\alpha_1$ is the temperature of air, $\alpha_2$ is the humidity of air and $\alpha_3$ is the flow rate of air which flows into a wiring or duct for the air-conditioning equipment.

Also, in this construction, the means for obtaining the first response characteristic may consist of the fluid measuring sensor 803 shown in FIGS. 7 and 9, and the means for obtaining the second response characteristic may consist of the temperature measuring sensor 802. Also, the system constituted by the fluid measuring sensor 803, the amplifier 87, the A/D converter 804 and the CPU 88 may form the means for obtaining the first response characteristic. Likewise, the system constituted by the temperature measuring sensor 802, the amplifier 87, the A/D converter 804 and the CPU 88 may form the means for obtaining the second response characteristic. Then, the means for comparing and processing the two response characteristics may consist of the CPU 88.

(Fourth Embodiment)

A fourth embodiment is directed to a method of measuring the flow rate of fluid of a different kind in the construction shown in the second embodiment. In the construction shown in the second embodiment, when the output from the respective sensors 802 and 803 are the same under the condition where the flow rate is 0, that is, when A=1 and B=0 in expression (1), even though the kind of fluid is different, the flow rate can be measured regardless of the kind of fluid if the physical property thereof is not extremely different.

This results from the fact that the thermal influence of fluid on the sensors 802 and 803 is caused by only the flow rate of fluid. That is, this results from canceling the influence related to the temperature of fluid and its physical property at the operating stage.

However, when measuring fluids, the physical properties of which are largely different, since a difference in the thermal influence of fluid on the thin-film material constituting the sensor is remarkable, a difference of the response characteristic corresponding to the flow rate results in a problem even though the flow rate is the same. For example, water and air cannot provide the same response characteristic. For solving this problem, some correction is required in measurement.

In the actual measurement of the flow rate, the output from the D/A converter 801 (refer to FIGS. 7 and 9) must be changed linearly in correspondence with the flow rate. That is, it is necessary that the output from the D/A converter 801 and the flow rate are related to a linear function having an inclination of 1 and an intercept of 0. This is an issue of software and therefore can be readily realized.

The inclination of the linear function depends on the kind of fluid. That is, the inclination of the linear function is different in accordance with the kind of fluid. Therefore, for example, in a case of measuring fluid A and in a case of measuring fluid B, the relationship between the output from the D/A converter 801 represented by the above linear function and the flow rate is changed appropriately so that the flow rate can be measured with accuracy regardless of the kind of fluid. In concrete, the inclination of the above linear function is changed in response to the kind of fluid, thereby being capable of executing the measurement of the flow rate not depending on the kind of fluid.

Also, even when the functional relationship between the output from the D/A converter 801 and the flow rate is not of a linear function, the functional relationship may be changed appropriately in accordance with fluid.

To realize the construction of this embodiment, the relationship between the output (for example, the output from the D/A converter 801) of the system in a given fluid and the flow rate is investigated in advance, and the correcting method may be stored in the CPU 88 or in a memory which is disposed separately. Then, it is allowed to correspond to the kind of fluid at the time of the measuring operation to perform the measuring operation.

The measuring principle of this embodiment can be also applied to a case shown in the third embodiment. That is, calibration is executed only for temperature, and the output from the D/A converter is corrected with reference to the output from the humidity measuring sensor provided separately with respect to a change in humidity. By doing so, an influence of factors other than the flow rate is removed as much as possible or removed to the allowable range to measure the flow rate.

(Fifth Embodiment)

A fifth embodiment is an example in which a known platinum sensor is used as a temperature measuring sensor, and the sensor shown in the first embodiment is used as a flow measuring sensor. This embodiment is different from the second embodiment in that the output from the platinum temperature sensor can be compared with the output from the flow rate measuring sensor by the A/D converter. Also, the operating method of the fluid measuring sensor is entirely identical with what is shown in the second embodiment.

Also, this embodiment is the same as the second embodiment in that the temperature measuring sensor is out of contact with the flow of fluid.

The fundamental operating method is the same as what is shown in the second embodiment. That is, if a state can be realized where the output from the platinum sensor which constitutes the temperature measuring sensor is converted into a digital signal by the A/D converter so as to be compared with the output (corresponding to the value of the area 104 of the waveform 102 in FIG. 10) from the fluid measuring sensor, the sensor may be operated in accordance with the procedure described in the second embodiment in the succeeding process.

In this embodiment, the function represented by FIG. 6 does not come to a linear function. This is because the characteristics of the temperature measuring sensor and the fluid measuring sensor to temperature are different from each other. In this embodiment, the temperature measuring sensor is of a platinum temperature sensor. However, other temperature sensors such as a semiconductor thermistor can be used.

(Sixth Embodiment)

In a sixth embodiment, an example of discriminating the kind of fluid by using a system with the construction of the second embodiment as shown in FIGS. 7 to 9 will be described.

Here, let us consider a case where the operation of the second embodiment is executed without flowing of fluid. This state is readily realized by closing both ends of a pipe shown in FIGS. 8 and 9. In this case, the output from the D/A converter 801 depends on the kind of fluid.

Figure 3:
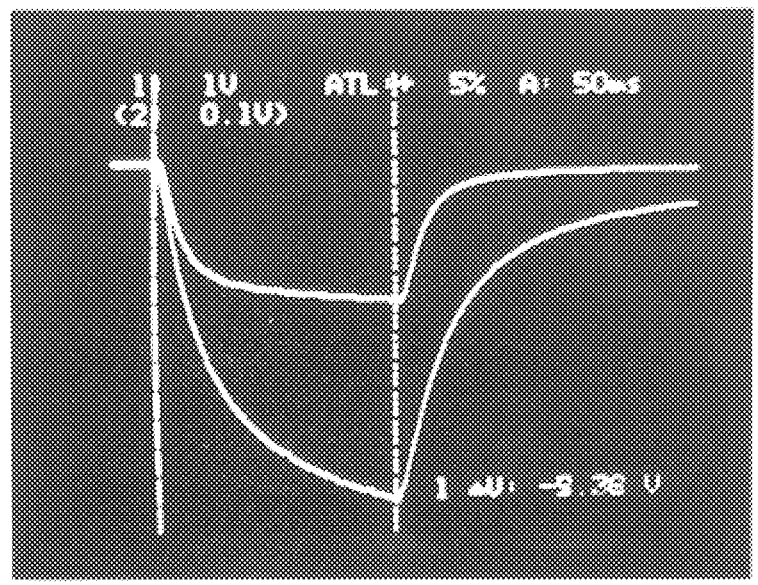
FIG. 3 is a diagram showing a photograph of an oscilloscope display.

This is because, if the kind of fluid is different, how to absorb heat from the diamond thin film is different as the thermal conductivity and the specific heat are different, with the result that the response waveform shown in FIGS. 3, 10 and 11 is different.

According to an experiment made by the inventors, if nitride gas and krypton gas flow at the same flow rate, and their flow rates are measured by the system shown in the second embodiment, it has been ascertained that there is a remarkable difference in output. This means that nitride gas and krypton gas can be discriminated, and is of a fact suggesting that it can be used as a gas sensor.

The operation as a gas sensor is fundamentally identical with a method of measuring the flow rate shown in the second embodiment. What is different from a case of measuring the flow rate is that a relationship between the kind of gas and the output from the D/A converter 801 is previously investigated, and the kind of gas is discriminated by referring an actually measured value to this relationship. Also, there is a difference in that fluid in contact with the sensor 803 is allowed to provide a constant flow rate.

Further, it is required that the temperature measuring sensor 802 is placed in a space which is tightly closed and is in contact with reference gas (for example, nitride gas or air). In this case, it is necessary that the temperature of reference gas is made identical with that of the environment or fluid to be measured. In concrete, it is required that the above tightly closed space is constituted with material having the high thermal conductivity such as aluminum, and a temperature measuring sensor 802 is located in the space.

According to the knowledge of the inventors, when operating as a gas sensor, an element most contributing to a difference in the output from the sensor is of the thermal conductivity of fluid. An element contributing subsequent to the thermal conductivity is a specific heat. Also, it is ascertained that the density or pressure of fluid affect the output.

Further, even when using not only gas but also liquid as fluid, it can be used as a sensor which discriminates the kind of fluid. In this case, the quantity of heat to be supplied to the heating element must be changed.

As described above, the sensor described in the second embodiment can function as a gas sensor or a liquid sensor as it is by somewhat modifying the arrangement of the temperature measuring sensor. For example, it can be used as a sensor for detecting that the concentration of a specific gas in air becomes a certain level or more. Also, it can be used as a sensor for measuring the humidity in air.

These operations can be executed in a state where they do not depend on the temperature of the fluid or environment, and therefore are very practical. In principle, even though material to be measured is of solid material, a difference in the thermal conductivity or specific heat of the material to be measured can be measured.

(Seventh Embodiment)

A seventh embodiment is directed to a construction for executing the measurement of the flow rate with accuracy in a still wider temperature range in the construction shown in the second embodiment. The second embodiment shows an example of using the functional relationship shown in expression (1) regardless of the output from the temperature measuring sensor, that is, regardless of the temperature of fluid.

This is on the assumption that the relational expression represented by expression (1) is satisfied regardless of the temperature of fluid. However, in the case where the temperature range in a use condition is remarkably wide, a case is considered where the relational expression represented by expression (1) is different in a low-temperature region and in a high-temperature region. In concrete, a case where the values of the constants A and B are different is considered.

There is considered a case where the quantity of heat to be supplied from the heating element must be changed in the low temperature region and the high temperature region. This is because the quantity of heat to be applied to the thin-film material must be different in the high-temperature region and the low-temperature region depending on the thermal capacity of the thin-film material and the kind of fluid to be measured, in order to obtain a required response characteristic.

In this case, there is considered a method of changing voltage to be applied to the heating element in accordance with the temperature of fluid and/or the temperature of the measurement environment. However, in this case, the measurement cannot be conducted by the method indicated by the second embodiment.

Hence, this embodiment is characterized in that the temperature range for measurement is divided into a plurality of sections, and the measurement is executed by the method shown in the second embodiment in one temperature range. For example, when the measurement is necessary in a range of −30° to 100° C., the temperature measuring range is divided in a plurality of sections such as −30° to 10° C., 10° to 50° C. and 50° to 100° C., and in each section, the measurement described in the second embodiment is executed.

In this case, in each temperature range, it is necessary to obtain the relational expressions represented by expressions (1) and (2). That is, it is necessary to conduct the calibration every temperature range. In each temperature range, if the relational expressions represented by expressions (1) and (2) is identical, it goes without saying that it is unnecessary to apply the method of this embodiment.

By applying the construction of this embodiment, an appropriate condition can be set in each temperature range, and the measurement of the flow rate or gas detection can be made with high accuracy in a wide temperature range. Also, the construction of this embodiment is characterized in that it can be practical by only storing the required condition in a memory. In concrete, the construction shown in FIGS. 7 to 9 can be utilized as it is.

(Eighth Embodiment)

In an eighth embodiment, a reference fluid and the temperature measuring sensor are brought in contact with each other to measure the fluid rate. In the construction as described in the second embodiment shown in FIGS. 7 to 9, the temperature measuring sensor 802 is not in direct contact with the flow 90 of fluid, but in contact with the fluid. That reason is to make the output from the temperature measuring sensor not influenced by the flow rate.

However, if the kind of the fluid to be measured is previously ascertained, the temperature measuring sensor is brought in contact with a reference fluid which is prepared separately, thereby being capable of measuring the temperature of the fluid to be measured or the temperature of the measurement environment.

In this case, the slit or opening shown by reference numeral 95 in FIG. 8 is not required. However, it is necessary to make the fluid having flow 90 identical in temperature with the fluid in contact with the temperature measuring sensor.

For example, when the flow rate of fluid is measured, the temperature measuring sensor for obtaining an output depending on the temperature of fluid and the fluid measuring sensor for obtaining an output depending on the flow rate and the temperature of fluid are disposed, thereby being capable of obtaining an output which depends on the flow rate not depending on the temperature of fluid or environment from the output from the temperature measuring sensor and the output from the fluid measuring sensor every measurement on the basis of the output from the temperature measuring sensor and the output from fluid measuring sensor which have been previously obtained.

In particular, the operation of the respective sensors can be enhanced in accuracy of measurement by using the response characteristic of the thin-film material in accordance with pulse-like heating. Also, by using the diamond thin film having a high thermal conductivity as a thin-film material, the flow rate can be measured over a wide measuring range.

Further, it can be operated as a gas sensor on the basis of the same principle as that of the measurement for the flow rate, thus being capable of realizing the gas sensor which is not influenced by the temperature of gas.

Although the present invention has been fully described by way of the preferred embodiments thereof with reference to the accompanying drawings, various changes and modifications will be apparent to those having skill in this field. Therefore, unless these changes and modifications otherwise depart from the scope of the present invention, they should be construed as included therein.

What is claimed is:

1. A measuring device comprising:
    a plurality of sensors each having a thin-film material,
        means for pulsedly heating said thin-film material,
        means for measuring a response characteristic of said thin-film material according to said pulsedly heating, in which among said plurality of sensors, at least one sensor is a temperature measuring sensor which functions to measure temperature of fluid and/or temperature of measurement environment, and at least another sensor is a fluid measuring sensor disposed in contact with the flow of said fluid; and
    means for processing an output from said temperature measuring sensor and an output from said fluid measuring sensor on the basis of a predetermined functional relationship,
    wherein said predetermined functional relationship is represented by the following expression (Ex. 2), using a function f(R) of the output R from said temperature measuring sensor and the output S from said fluid measuring sensor, where F is a value of flow rate or flow velocity of said fluid, $$F = f(R) - S \qquad \text{(Ex. 2)}.$$

2. The device of claim 1 wherein the output from said temperature measuring sensor and the output from said fluid measuring sensor are processed according to the predetermined functional relationship, to obtain a value corresponding to flow rate or flow velocity of said fluid which does not depend on the temperature of said fluid and/or the temperature of the measurement environment.

3. The device of claim 1 wherein the output from the respective sensors is based on the response characteristic of said thin-film material according to said pulsedly heating.

4. The device of claim 1 wherein said temperature measuring sensor and said fluid measuring sensor have the substantially same characteristic.

5. The device of claim 1 wherein a fluid in contact with said temperature measuring sensor has always a constant flow rate.

6. A measuring device comprising:
    a plurality of sensors each having a thin-film material,
        means for pulsedly heating said thin-film material,
        means for measuring a response characteristic of said thin-film material according to said pulsedly heating, in which among said plurality of sensors, at least one sensor is a temperature measuring sensor which functions to measure temperature of a reference fluid and/or temperature of measurement environment, and at least another sensor is a fluid measuring sensor disposed in contact with fluid to be measured; and
    means for processing output from said temperature measuring sensor and output from said fluid measuring sensor on the basis of a predetermined functional relationship,
    wherein the predetermined functional relationship is represented by the following expression (Ex. 2), using a function f(R) of the output R from said temperature measuring sensor and the output S from said fluid measuring sensor, where F is a value of a physical property of said fluid to be measured, $$F = f(R) - S \qquad \text{(Ex. 2)}.$$

7. The device of claim 6 wherein a specific fluid to be measured is discriminated according to an output from said processing means.

8. A measuring device comprising:
    at least one first sensor for measuring a flow rate or flow velocity of fluid which flows in contact with a thin-film material according to a response characteristic of said thin-film material to pulse-like heating;
    at least one second sensor for measuring a temperature of fluid and/or a temperature of measurement environment; and
    means for processing an output from said first sensor and an output from said second sensor on the basis of a predetermined functional relationship to obtain a value of the flow rate or the flow velocity which does not depend on the temperature of said fluid and/or the temperature of the measurement environment,
    wherein said predetermined functional relationship is represented by the following expression (Ex. 2), using a function f(R) of the output R from said second sensor and the output S from said first sensor, where F is a value of the flow rate or the flow velocity of said fluid, $$F = f(R) - S \qquad (\text{Ex. 2}).$$

9. A measuring device comprising:

a plurality of sensors each having a thin-film material, means for pulsedly heating said thin-film material, means for measuring a response characteristic of said thin-film material according to said pulsedly heating, in which among said plurality of sensors, at least one sensor is a temperature measuring sensor which functions to measure temperature of fluid and/or temperature of measurement environment, and at least another sensor is a fluid measuring sensor disposed in contact with the flow of said fluid; and means for processing an output from said temperature measuring sensor and an output from said fluid measuring sensor on the basis of a predetermined functional relationship, wherein said temperature measuring sensor and said fluid measuring sensor are substantially equal in characteristic to each other, and said predetermined functional relationship is represented by the following expression (Ex. 1) using the output R from said temperature measuring sensor and the output S from said fluid measuring sensor, where A and B are constants, and F is a value of flow rate or flow velocity of said fluid, $$S = AR + B - F \qquad (\text{Ex. 1}).$$

10. A measuring device comprising:

a plurality of sensors each having a thin-film material, means for pulsedly heating said thin-film material, means for measuring a response characteristic of said thin-film material according to said pulsedly heating, in which among said plurality of sensors, at least one sensor is a temperature measuring sensor which functions to measure temperature of a reference fluid and/or temperature of measurement environment, and at least another sensor is a fluid measuring sensor disposed in contact with fluid to be measured; and means for processing output from said temperature measuring sensor and output from said fluid measuring sensor on the basis of a predetermined functional relationship, wherein said temperature measuring sensor and said fluid measuring sensor are substantially equal in characteristic to each other, and the predetermined functional relationship is represented by the following expression (Ex. 1) using the output R from said temperature measuring sensor and the output S from said fluid measuring sensor, where A and B are constants, and F is a value of a physical property of said fluid to be measured, $$S = AR + B - F \qquad (\text{Ex. 1}).$$

11. A measuring device comprising:

at least one first sensor for measuring a flow rate or flow velocity of fluid which flows in contact with a thin-film material according to a response characteristic of said thin-film material to pulse-like heating;

at least one second sensor for measuring a temperature of fluid and/or a temperature of measurement environment; and means for processing an output from said first sensor and an output from said second sensor on the basis of a predetermined functional relationship to obtain a value of the flow rate or the flow velocity which does not depend on the temperature of said fluid and/or the temperature of the measurement environment, wherein said first sensor and said second sensor are substantially equal in characteristic to each other, and said predetermined functional relationship is represented by the following expression (Ex. 1) using the output R from said second sensor and the output S from said first sensor, where A and B are constants, and F is a value of the flow rate or the flow velocity of said fluid, $$S = AR + B - F \qquad (\text{Ex. 1}).$$

* * * * *